US012706440B2

(12) United States Patent
Pruitt et al.

(10) Patent No.: US 12,706,440 B2
(45) Date of Patent: Aug. 11, 2026

(54) SWITCHABLE LOW PULSE RATE AND HIGH PULSE RATE LASER DRIVER

(71) Applicant: Cold Laser Therapeutics, LLC, Arvada, CO (US)

(72) Inventors: Ralph Pruitt, Arvada, CO (US); Greg Richardson, Essex, MD (US)

(73) Assignee: Cold Laser Therapeutics, LLC, Arvada, CO (US)

( * ) Notice: Subject to any disclaimer, the term of this patent is extended or adjusted under 35 U.S.C. 154(b) by 262 days.

(21) Appl. No.: 18/281,827

(22) PCT Filed: May 11, 2023

(86) PCT No.: PCT/US2023/021847
§ 371 (c)(1),
(2) Date: Sep. 13, 2023

(87) PCT Pub. No.: WO2023/220248
PCT Pub. Date: Nov. 16, 2023

(65) Prior Publication Data

US 2025/0087967 A1 Mar. 13, 2025

Related U.S. Application Data

(60) Provisional application No. 63/341,793, filed on May 13, 2022.

(51) Int. Cl.
*H01S 5/062* (2006.01)
*A61N 5/067* (2006.01)
(Continued)

(52) U.S. Cl.
CPC .......... *H01S 5/06233* (2013.01); *A61N 5/067* (2021.08); *A61B 2017/00194* (2013.01);
(Continued)

(58) Field of Classification Search
CPC ................ H01S 5/06233; A61N 5/067; A61N 2005/0626; A61N 2005/0651;
(Continued)

(56) References Cited

U.S. PATENT DOCUMENTS 5,624,435 A 4/1997 Furumoto et al.
6,632,219 B1 * 10/2003 Baranov ........... A61B 18/0218 606/22

(Continued)

OTHER PUBLICATIONS

International Search Report and Written Opinion from PCT/US2023/021847, US International Searching Authority, mailed on Jul. 31, 2023, 6 pages.

*Primary Examiner* — Ahmed M Farah
(74) *Attorney, Agent, or Firm* — FisherBroyles, LLP; Gregory T. Fettig; Russell Manning

(57) ABSTRACT

Systems and methods herein provide for a diode laser system that improve cold laser therapy. One cold laser therapy device includes a laser diode operable to propagate laser pulses towards a person's skin, a first driver operable to drive the laser diode to propagate the laser pulses within a first range of laser pulse rates, and a second driver operable to drive the laser diode to propagate the laser pulses within a second/higher range of laser pulse rates. The device also includes a controller operable to process an instruction to tune a laser pulse rate of the laser diode from the first range of the laser pulse rates to the second range of the laser pulse rates, to disable the first driver in response to the instruction, and to enable the second driver in response to the instruction.

17 Claims, 24 Drawing Sheets

(51) Int. Cl.
*A61B 17/00* (2006.01)
*A61B 18/00* (2006.01)
*A61N 5/06* (2006.01)

(52) U.S. Cl.
CPC ............... *A61B 2017/00221* (2013.01); *A61B 2018/00642* (2013.01); *A61B 2018/00702* (2013.01); *A61N 2005/0626* (2013.01); *A61N 2005/0651* (2013.01)

(58) Field of Classification Search
CPC ........... A61B 2017/00194; A61B 2017/00221; A61B 2018/00642; A61B 2018/00702
USPC ............................................................ 607/89
See application file for complete search history.

(56) References Cited

U.S. PATENT DOCUMENTS 8,236,036 B1 * 8/2012 Frost .................... A61N 5/0616 128/898
2004/0158300 A1 8/2004 Gardiner
2006/0224218 A1 10/2006 Tucek et al.
2012/0010686 A1 1/2012 Shanks et al.
2018/0369602 A1 * 12/2018 Tichauer .............. A61N 5/0616
2021/0196977 A1 * 7/2021 Zhang .................. A61N 5/0616
2025/0087967 A1 * 3/2025 Pruitt .................. H01S 5/06233

* cited by examiner

Loop Filter for PLL

C7 IN
C53
270pF 10%
GND
R69
430 1%
C57
0.027uF 20%
R67
390 1%
C54
200pF 5%
GND
R68
390 1%
C55
390pF 10%
GND
VIUNE OUT

FIG. 10

SWITCHABLE LOW PULSE RATE AND HIGH PULSE RATE LASER DRIVER

CROSS REFERENCE TO RELATED APPLICATIONS

This patent application is a 371 National Stage Application of PCT/US23/21847, filed May 11, 2023, which claims priority to, and thus the benefit of an earlier filing date from, U.S. Provisional Patent Application No. 63/341,793 (filed May 13, 2022), the contents of which are hereby incorporated by reference.

BACKGROUND

Cold laser therapy uses laser light with specific properties to treat pain and injuries. A cold laser generally includes wavelengths, intensities, and durations of treatments that do not damage tissue. Most cold lasers are built to emit pulse waves of laser radiation. The pulse design allows the device to emanate higher peak power levels, which have been linked to the better therapeutic outcomes, while remaining safe.

Cold laser therapy typically uses infrared light, which cannot be seen or felt, to reduce inflammation, swelling and pain. Because light at these wavelengths is capable of inducing vibrations in atoms and molecules, it is often referred to as heat. Cold laser therapy is referred to as "cold" because, below 5 mW optical power, it does not provide enough energy to be perceived as heat. Some cold laser therapies use a wavelength of about 635 nm, though this has been extended recently to the near-infrared spectrum between 800 nm and 860 nm. Some manufacturers even build devices that operate between 600 nm and 680 nm.

The anti-inflammatory effects of the infrared light are believed to work through several pathways at the cellular level. Unlike modalities, such as cortisone injections and non-steroidal anti-inflammatory pills, cold laser therapy does not suppress inflammation, but rather stimulates a body's cells to reduce inflammation, swelling, and pain.

Most cold laser therapy treatment devices operate well under 10 Khz, or 10,000 pulses per second. As the efficacy of cold laser therapy is proven out, higher pulse-rate treatment regimens may be desirable, but such systems can add considerable design complexity, part counts, and regulatory hurdles, which add to cost of a device and can stifle investigation of new treatment regimes.

SUMMARY

Systems and methods herein provide for a diode laser system that improve cold laser therapy systems, protocols, portability, and outcomes. The present embodiments are directed to a low-cost, hybrid laser driver circuit with integrated low-pulse rate and high-pulse rate laser diode drivers, such that pulse rates from direct current (DC, e.g., zero Hz) to multiple Gigahertz can be supported while delivering laser pulses of consistent intensity. In particular, the present embodiments are desirable for medical laser and cold laser therapies, and additional methods are described for integration into telehealth, remote treatment, virtual reality (VR) systems, artificial intelligence (AI) patient interaction systems, as well as outcome analysis systems, using wired and wireless communications, onboard memory, sensors (such as inertial measurement units, or "IMUs"), and over-the air updating for both embedded systems and treatment protocols.

A high frequency/low frequency laser driver circuit described herein is a hybrid driver based on a low modulation frequency laser driver that has been combined with a high modulation frequency laser driver circuit (e.g., such as those used for laser communications) in such a way that any laser diode pulse rate inside a desired rate range can be controlled by a low or high frequency driver in one device to deliver consistent laser optical power across that range. The goal in this design is a low-cost driver circuit that allows both the low frequency driver circuit and the high frequency driver circuit to coexist in the same driver, and share features to deliver consistent and safe optical power, while having the ability to run off a shared MCU which can also control the power planes of various subcircuits to conserve power.

Additionally, because the embodiments herein are particularly suitable for cold laser therapy devices, additional methods are described to integrate wired debug and programming of embedded systems, wireless communication, onboard memory, over the air updating for both embedded systems and cold laser therapy protocols, inertial measurement units, and other sensing capabilities, for the purpose using the device in telehealth, remote treatment, VR systems, AI patient interaction systems, and/or outcome analysis systems.

In one embodiment, a hybrid low-pulse rate/high-pulse rate laser driver circuit can be pulsed at accurate and selectable pulse rates from 0 Hz to over 4 Gz while delivering the consistent, high intensity laser pulses required for the most therapeutic benefit in the shortest treatment time. The hybrid driver circuit has reduced part-count and footprint, resulting in lower costs and more design flexibility.

In another embodiment, the hybrid driver is composed of multiple connected elements. A first element is laser diode of a suitable wavelength for cold laser therapy, having a common photodiode cathode, and a laser diode anode. A second element uses bipolar junction transistors (BJTs), resistors, capacitors, and Zener diodes, to provide: a current source; biasing to deliver consistent, high optical power pulses across a wide range of modulations; setpoint summing a modulation input; photodiode current sensing during laser operation (e.g., optical power sensing and error signaling): 5) a feedback loop and modulation tracking; and 6) a limit circuit. A microcontroller unit (MCU) can directly drive this element to deliver consistent, high optical power laser pulses at arbitrary/tunable rates below 100-200 Mhz (e.g., the clock rate of the MCU).

A phase-locked loop (PLL) system is implemented using (e.g., on a functional level) a fractional-N PLL with an integrated voltage controlled oscillator (VCO) chip (e.g., using an Analog Devices HMC832) and various filtering capacitors and resistors. The PLL system can drive high pulse rate signals (e.g., up to 3 GHz) of arbitrary (fractional N) frequencies when provided with parameters from an MCU via a serial peripheral interface (SPI).

A high-frequency laser driver circuit (e.g., a Micrel SY88422 Driver chipset), which is driven by the PLL system, delivers a differential, floating, high pulse rate driver signal across the laser diode.

The hybrid design can have the central element switched to operate as a low pulse rate laser diode driver, and/or to operate as the setpoint (fixed current source) around which the high pulse rate signal from the high frequency laser driver circuit modulates. This high rate rejects changes in the setpoint fixed current course, delivers consistent, high optical power pulses across a wide range of high pulse rate modulations, and retains the limit circuit capabilities. One goal in this approach is to allow both the low frequency driver circuit and the high frequency driver circuit to coexist in the same driver circuitry and be controlled by the same MCU, while implementing a low chip count device constructed from commodity-priced parts.

In another embodiment, the resulting laser driver and devices are designed further to be integrated into telehealth, remote treatment, VR systems, AI patient interaction systems and/or outcome analysis systems, with onboard sensors such as IMUs (e.g., for reporting orientation), and wireless flow of treatment information both to and from the device. The wide range of potential therapeutic pulse rates, and combinations thereof, of the embodiments herein provide for use and treatment protocol information (e.g., for outcome analysis) that are advantageous over the prior art.

In another embodiment, a cold laser therapy device includes a laser diode operable to propagate laser pulses towards a person's skin, a first driver operable to drive the laser diode to propagate the laser pulses within a first range of laser pulse rates (e.g., between about zero Hz and 50 MHz), and a second driver operable to drive the laser diode to propagate the laser pulses within a second range of laser pulse rates (e.g., between about 50 MHz and 4 GHz). The second range of laser pulse rates is higher than the first range of laser pulse rates. The device also includes a controller (e.g., an MCU) operable to process an instruction to tune a laser pulse rate of the laser diode from the first range of the laser pulse rates to the second range of the laser pulse rates, to disable the first driver in response to the instruction, and to enable the second driver in response to the instruction. In some embodiments, a phase locked loop controller is operable to drive the second driver, and to maintain a constant pulse rate within the second range of laser pulse rates.

In some embodiments, the controller is further operable to receive another instruction to tune the laser pulse rate of the laser diode from the second range of the laser pulse rates to the first range of the laser pulse rates, to disable the second driver in response to the instruction, and to enable the first driver in response to the instruction. In some embodiments, the first driver comprises a feedback circuit that is operable to control optical energy of the laser pulses from the laser diode (e.g., to less than about 6 milliwatts).

In some embodiments, the system includes a wireless communication module operable to provide remote control to the device, and/or to provide an interface for at least one of upgrading firmware to the device and communicating with a caregiver.

Additionally, the various embodiments disclosed herein may be implemented in a variety of ways as a matter of design choice. For example, some embodiments herein are implemented in hardware, whereas other embodiments may include processes that are operable to implement and/or operate the hardware. Other exemplary embodiments (e.g., methods and computer readable media relating to the foregoing embodiments) may be described below. The features, functions, and advantages that of been discussed can be achieved independently in various embodiments or may be combined in yet other embodiments, further details of which can be seen with reference to the following description and drawings.

BRIEF DESCRIPTION OF THE DRAWINGS

FIG. 10 illustrates one exemplary loop filter for phase-locked loop circuitry.

DETAILED DESCRIPTION OF THE DRAWINGS

The figures and the following description illustrate specific exemplary embodiments. It will thus be appreciated that those skilled in the art will be able to devise various arrangements that, although not explicitly described or shown herein, embody certain principles that are included within the scope of the embodiments. Furthermore, any examples described herein are intended to aid in understanding these principles, and are to be construed as being without limitation to such specifically recited examples and conditions. As a result, the embodiments are not limited to the specific examples described below.

Technical specifications for cold laser therapy diode embodiments herein generally include: a collimated laser with a collimating lens; laser wavelengths near 635 nm as hemoglobin interacts with laser light of 634.7-634.8 and/or in the visible range 300 nm to 800 nm; and a 3 pin model laser pin diode; and a controller for controlling optical power (e.g., intensity).

The laser diode may be 1 cm diameter, 5-6 mm in length, incorporate heat sinks, have a class 3 classification, and have relatively low power (e.g., 8 mW). Using too much power can result in failure, so a diode that is to be used at 5 mw is likely rated at 8 mW.

Cold laser therapy protocols typically specify 30-50 Mhz pulse rates, but advances in the technology see reasons to employ upwards to about 4 Ghz, with a 40-60% modulation duty cycle and relatively small transients in optical power. If the cold laser therapy diode is rated at 635 nm, the error is typically +/−1%.

Figure 1:
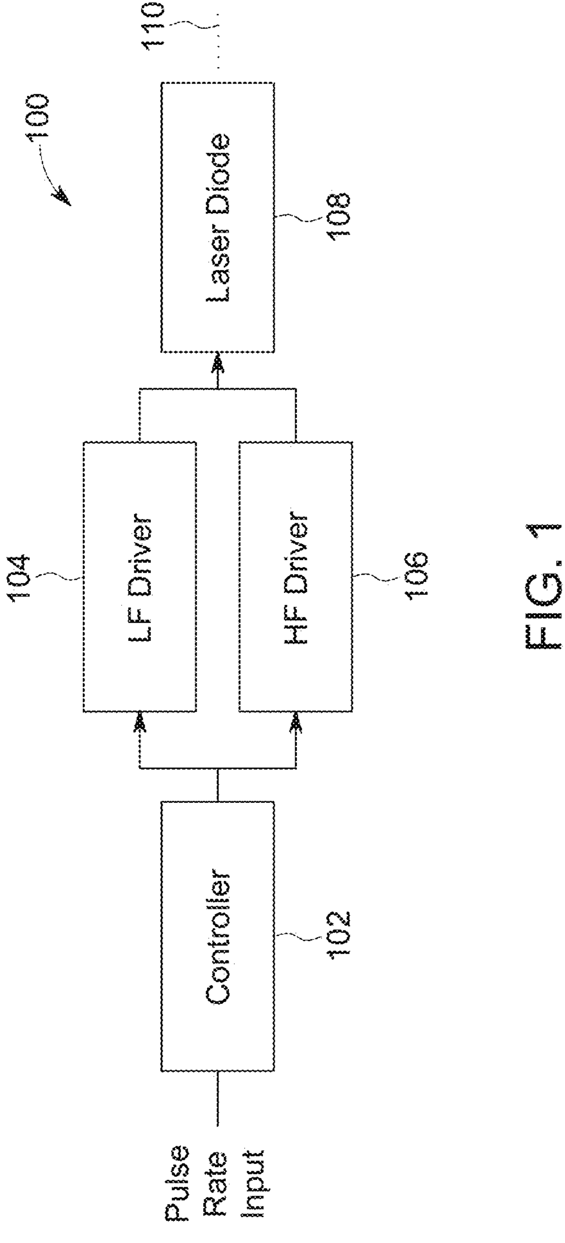
FIG. 1 is a block diagram of an exemplary laser diode system having a tunable pulse rate.

With this in mind, FIG. 1 is a block diagram of a laser diode system 100 having a pulse rate that is tunable within multiple ranges of pulse rates. For example, the laser diode system 100 may include a laser diode 108 that is operable to propagate laser light. In some embodiments, that laser light may be limited to about 5 mW such that it is suitable for cold laser therapy uses (i.e., a medical procedure). The laser diode system 100 may also include a first/low-frequency driver 104 operable to drive the laser diode 108 to propagate laser pulses 110 at a first range of pulse rates (e.g., between about 0 Hz and 50 MHz). That is, the first driver 104 may drive the laser diode 108 to generate laser pulses 110 at a pulse rate that is tunable within the first range of laser pulse rates that is lower than a range of pulse rates of a second/high frequency driver 106.

As some cold laser therapies may need higher pulse rates that are outside the range of the first driver 104, the laser diode system 100 may use the second/high-frequency driver 106 to drive the laser diode 108 to propagate the laser pulses 110 at a second range of laser pulse rates that is higher than the first range of laser pulse rates (e.g., between about 50 MHz and 4 GHz).

To tune between the first and second pulse rates, the laser diode system 100 may also include a controller 102 (e.g., an MCU) operable to receive an instruction (e.g., a pulse rate input) to tune the laser pulse rate of the laser diode 108 from the first range of the laser pulse rates to the second range of the laser pulse rates, and vice versa. For example, the laser diode system 100 may be included in a handheld device for use in cold laser therapy. And a user holding the device may wish to increase the pulse rate of the laser diode 108. The user may change the pulse rate by selecting a new pulse rate via an input module (e.g., a knob, frequency selection module, etc.). And, in response to the instruction, the controller 102 may disable the first driver 104 to enable the second driver 106. With the second driver 106 engaged, the laser diode system 100 may output laser pulses 110 at the second range of laser pulse rates as desired. Similarly, when a lower pulse rate is desired (i.e., one that falls within the lower range of laser pulse rates), the controller 102 may disable the second driver 106 and engage the first driver 104 (e.g., based on an instruction by the user).

It should be noted that the embodiment herein is not intended to be limited to two drivers 104 and 106 and/or a single laser diode 108. Some embodiments may be configured in other ways that implement a plurality of different pulse rate ranges. And some embodiments including those shown and described below may include more than one laser diode 108 (e.g., with each laser diode 108 being driven by its own plurality of drivers).

In some embodiments, the first driver 104 includes a feedback circuit that is operable to control optical energy of laser pulses 110 from the laser diode 108 at a predetermined level. For example, the first driver 104 may include a photo diode that is operable to determine an optical intensity of the laser diode 108. And a signal from the photo diode may be used to control the amount of optical intensity that the laser diode 108 outputs to ensure that the laser diode 108 does not exceed a predetermined optical intensity (e.g., so as to remain suitable for cold laser therapy purposes of around 5 milliwatts).

In some embodiments, the laser diode system 100 includes a phase locked loop (PLL) controller operable to drive the second driver 106 so as to maintain a constant pulse rate within the second range of laser pulse rates. For example, when the laser diode 108 is operable to pulse laser light in the second range of pulse rates, the PLL may ensure that the second driver is "locked in" to any desired pulse rate within that range so that the laser diode system 100 may deliver laser pulses 110 at that desired rate.

Figure 2:
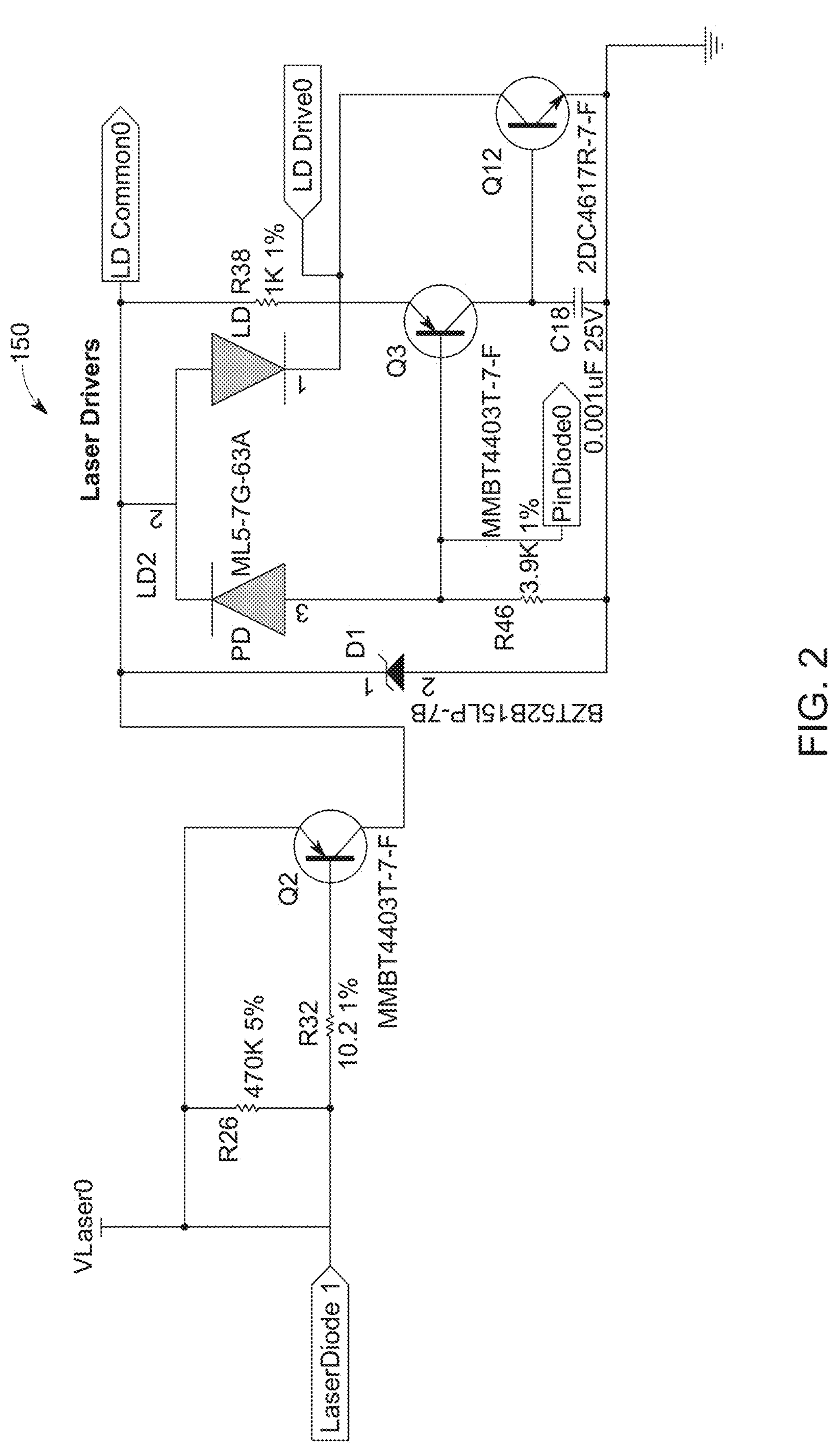
FIG. 2 illustrates one exemplary embodiment of a low pulse rate laser driver, using a ML5-7D-63 paired laser diode and photodiode module with a modulation pin Laser Diode 1, and high-frequency differential modulation pins LD Common0 and LD Drive0.

FIG. 2 illustrates one non-limiting, exemplary low pulse rate laser driver 150 (e.g., the driver 104). This embodiment is not to be taken as limiting in respect to selection of circuit elements, including diode and transistor types, as other configurations and choices consistent with various laser diodes and/or photodiodes are possible. The voltage at VLaser0 is selected to be consistent with the voltage requirements of the paired laser diode module LD2. In this embodiment, the bipolar junction transistors Q2 and Q3 are PNP, whereas Q12 is NPN. Transistor Q2 controls the current flow to paired photodiode PD and a laser diode LD. Q2 is gated by the external control voltage LaserDiode1, which is some combination of the external setpoint and modulation signal. The voltage at VLaser0 is the "on-off" switch for LD2, and can be controlled by an MCU, external switch, or the like.

Internally, no current flows through LD except through transistor Q12. Thus Q12 is the current controller for the laser diode LD, with the voltage at the base serving as the feedback signal input for the current controller. PinDiode0 is a voltage "pick off" sensor for a current control error signal, which can be sent to the MCU (e.g., the controller 102), and external display, a meter, or the like. The feedback voltage at PinDiode is proportional to the current flowing through PD, which is, in the lasing regions of LD, proportional to the optical intensity and energy of LD. PinDiode0 is both the error signal used to track the modulation signal, and an error signal that limits the optical energy of LD to the chosen optimum, irrespective of Zener diode limit circuit D1.

Alternatively or additionally, any current flowing through Q2 can flow through the photodiode PD and resistor R46, through resistor R38 and Q3 (e.g., depending on the voltage to the base for Q3), or through the Zener diode D1.

The Zener diode D1, resistors R46, R38, R26, and R32, the capacitor C18, and the photodiode PD act to bias the circuit. The voltage across D1 determines the maximum voltage from LD_Common0 and ground. R46 limits the current through PD, and the voltage divider between them biases the base of Q3. R38 both acts to limit the current of Q3 and biases its emitter. R26 biases the base of Q2, while the combination of R26 and R32 can be used to determine the input impedance seen by external circuitry driving the input of LaserDiode1.

Because operating at the maximum optical intensity/energy is generally preferable for cold laser applications, the device may select and/or tune the circuit elements D1, R26, R32, R46, R38, and C18 such that when LaserDiode1 is held at ground, the optical energy from the laser diode LD is as high as possible for safe operation. Low pulse rate operation is typically 0 Hz (i.e., with LD constant optical intensity and energy output) up to the "switchover pulse rate" of about 50 MHz where the device is operated in high pulse rate mode. For low pulse rate operation, the configuration in FIG. 2 allows for switching mode (i.e., a square wave) operation of the BJTs by modulating LaserDiode1 between ground and the voltage. Thus, selecting BJTs suitable for this mode is desirable.

When a switching modulation signal is applied to the external input LaserDiode1, Q2 provides modulated power to the rest of the circuit at LD_Common0 consistent with the modulation input. When the voltage LD_Common0 goes high, assuming C18 has had time to drain through R46, the PNP transistor Q3 is in the cutoff region while the NPN transistor Q12 is in the saturation region. Q3 is "off" because the PD is flowing very little current. Thus, R46 has very little voltage across it and is effectively a short to ground for the base. This means that the base of Q12 is pulled up along with the collector of Q3, and thus Q12 is "on". This allows the current through LD to exceed the threshold current and the diode lases. As current through PD begins to flow, the error voltage signal PinDiode0 across R46 rises. The feedback control action on the error signal occurs because current flowing through R38 drives Q3, and more specifically its collector, lower, which in turn drives the voltage of the base of Q12 lower and throttles the current.

When the voltage at LD_Common0 is off but there is sufficient charge in C18, the collector to base pathway through the PNP transistor Q3 is a forward biased PN junction diode, and current flows until the diode voltage of the junction is reached. This current flow has an RC time constant of approximately R46*C18, the resistance being measured in ohms and the capacitance being measured in farads. As the modulation frequency goes up, the average charge in C18, and thus the average voltage at the base of Q12, increases. Since the error signal PinDiode0 cannot go lower than the voltage at the base minus the diode drop across the collector and base of Q3, there is effectively a low pass filter at roughly 1/(2π*R46*C18) Hz on the error signal, and above some high frequency, Q12 remains on. And the driver current is at the value set by the Zener diode. C18 is selected such that, in combination with biasing and current limiting resistor R46, the corner frequency is well above any low pulse rate modulation signal that will be applied to LaserDiode1.

Figure 3:
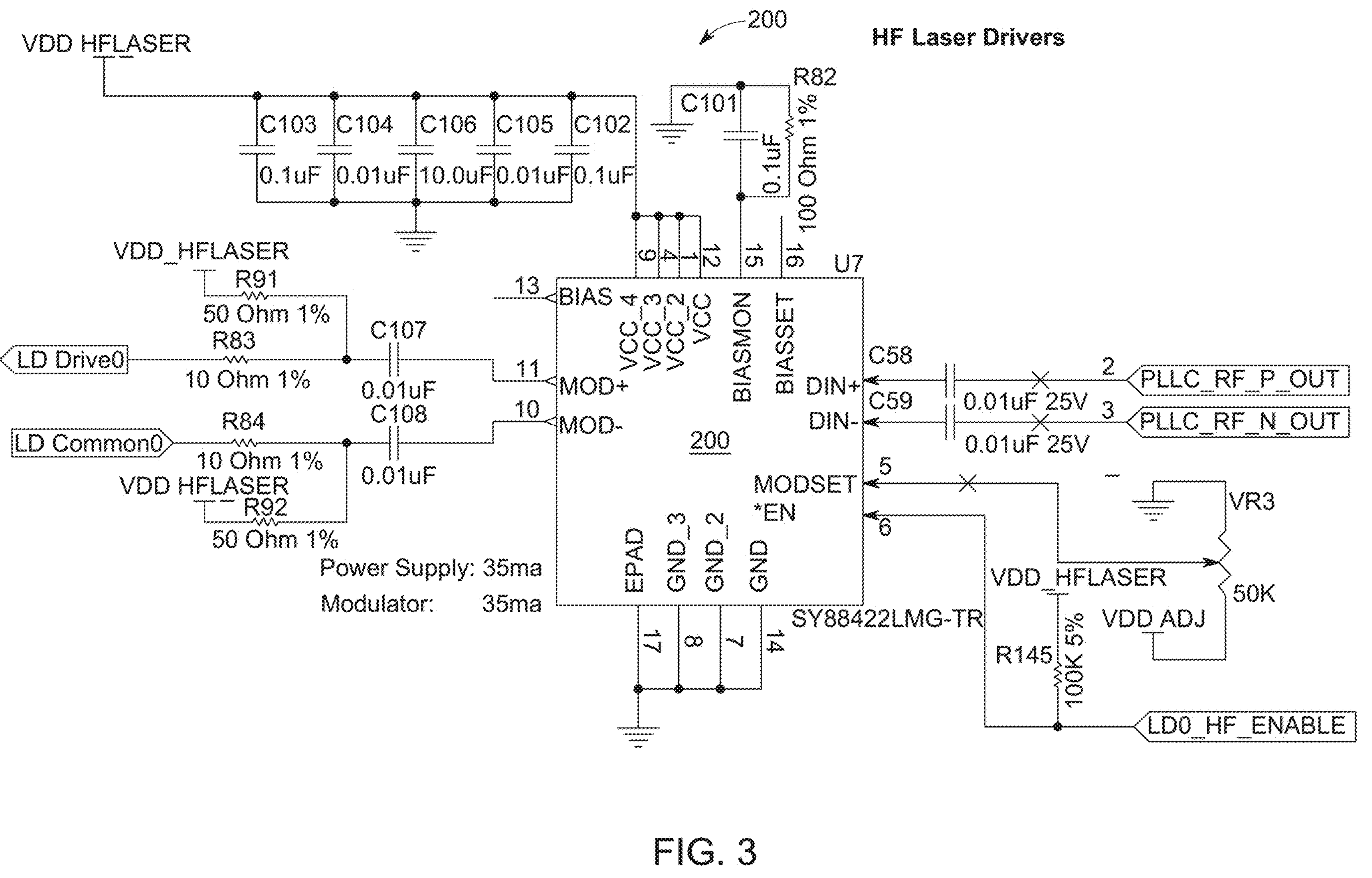
FIG. 3 illustrates one exemplary embodiment of a high pulse rate differential laser driver subsystem using a Micrel SYS88422L chip, with modulation inputs PLLC RF P_OUT and PLLC RF N_OUT, and differential modulation outputs LD Drive0 and LD Common0.

FIG. 3 illustrates one non-limiting, exemplary high pulse rate laser driver system 200 (e.g., the driver 106) that, at DC, provides a floating drive rate signal. FIG. 3 is not to be taken as limiting in respect to selection of circuit elements. In one embodiment, the Micrel SY88422LMG-TR chip 202 may be used as a high frequency laser driver suitable for frequencies in the tens of millions to billions of pulses per second, intended for use, among other things, in laser communications devices. Technical specifications for the SY88422 chip include a 35 mA power supply current, a typical operation up to 4.25 Gbps, a modulation current up to 90 mA, and bias current up to 100 mA.

Both the differential inputs PLLC_RF_P_OUT and PLLC_RF_N_OUT and both the differential outputs LD_Common0 and LD_Drive0 are floated with capacitors such that, at sufficiently low frequencies, the LD_Drive circuit (e.g., the low pulse rate laser driver 150) can be enabled or disabled by applying a voltage to LDO_HF_ENABLE, which can be controlled via the MCU, external switch, or the like.

The pre-Driver in the chip 202 can be thought of as an operational amplifier with rails set high by LDO_HF_ENABLE and low by the MODSET voltage, which can be trimmed via the potentiometer VR3 to adjust the differential output voltage applied across MOD+ and MOD− of the chip 202.

When the chip 202 is enabled and the differential inputs are driven with a quality, low power modulation signal at pulse rates sufficiently high that differential chip outputs MOD+ and MOD-pass through the high pass filters (i.e., R91, R83, C107, and R84, R92, C108), the chip 202 is capable of driving a laser diode connected across LD_Drive0 and LD_Common0 at high power at that same frequency. The achieved duty cycle, especially at the highest frequencies, is a function of the PD-LD element specifications. The frequency-dependent load impedances are L_Drive0 and LD_Common0, which exists when the circuit is disabled are selected using R91, R83, and C107, and R84, R92, and C108.

Figure 4:
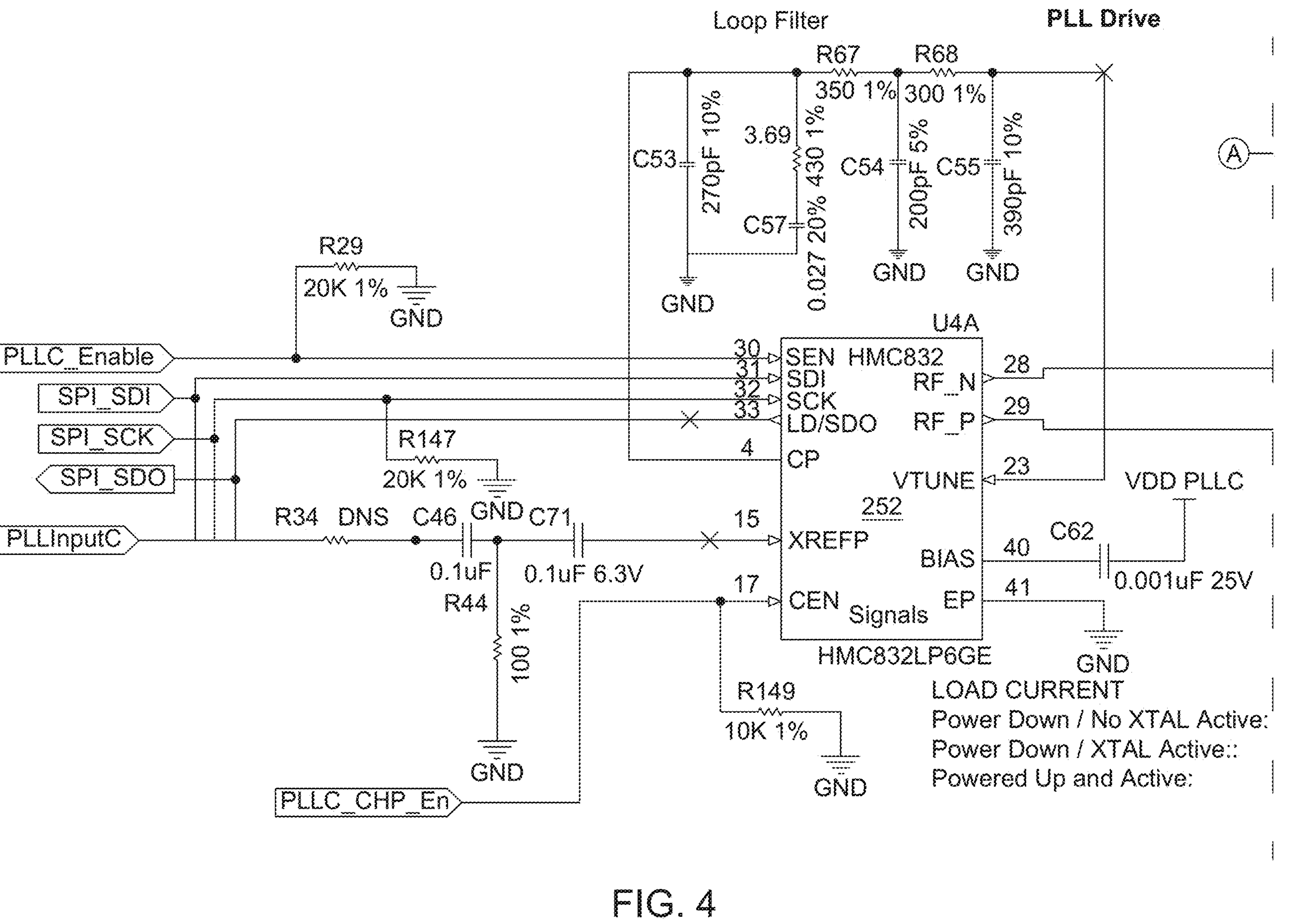
FIG. 4 illustrates one exemplary embodiment of a PLL modulation drive (lcft) subsystem and its power configuration (right), using Analog Devices HMC832 fractional-N PLL with an integrated VCO.
Figure 4:
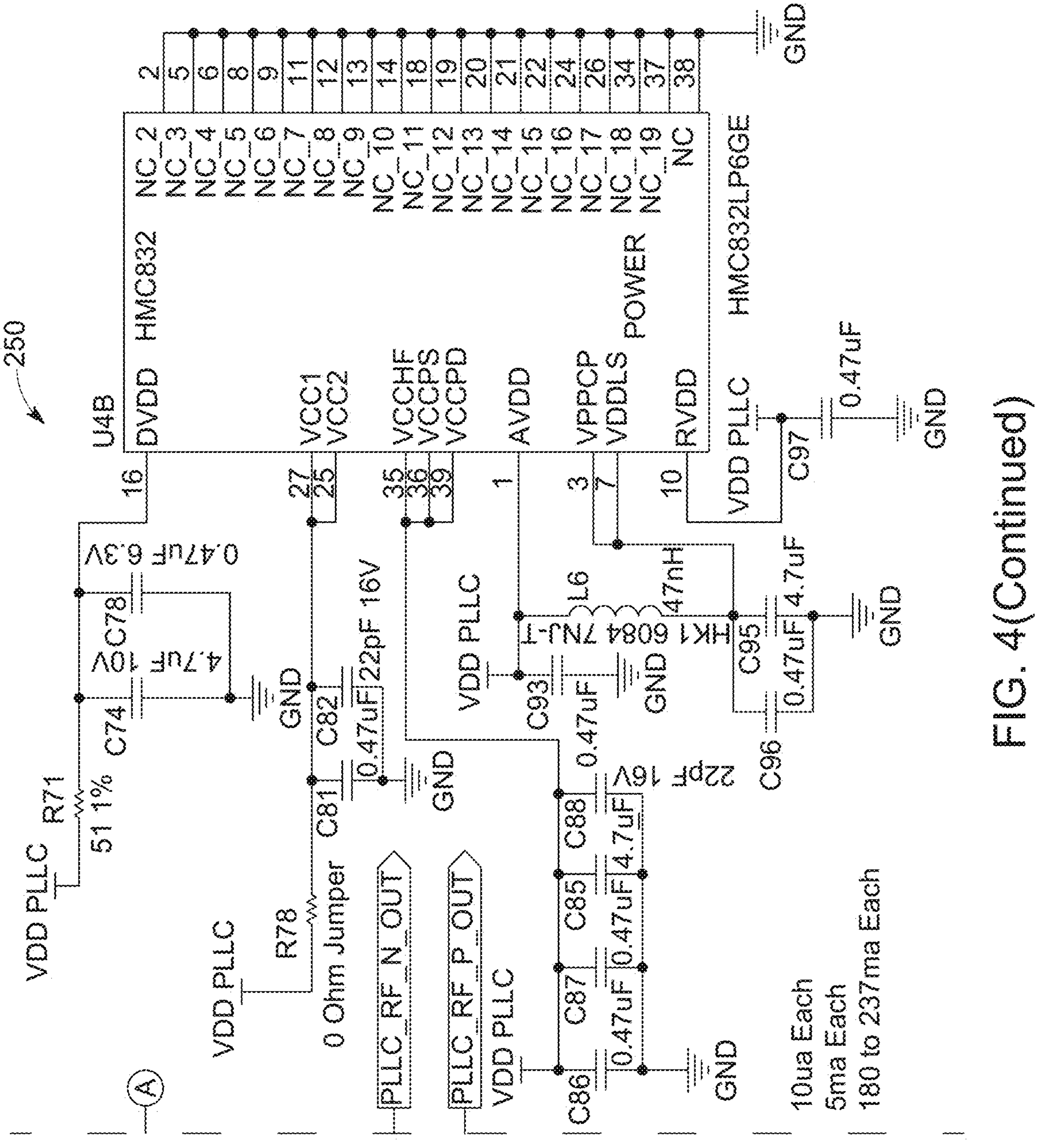

FIG. 4 illustrates one non-limiting, exemplary high pulse rate fractional PLL drive 250 with an integrated VCO modulation signal generator 252. FIG. 4 is not to be taken as limiting in respect to selection of circuit elements. The inputs of the PLL Drive 250 include the common SPI pins-SDI, SCK, SDO, SEN driven by PLLC_Enable, as well as PLLInputC. SDI, SCK, SDO, and SEN can be used to directly program registers that either directly control the PLL 252, or allow the PLL 252 to program the VCO indirectly. The clock signal into PLLCInputC may originate from a crystal.

The VCO tunes to the selected fundamental frequency (e.g., 1.5 GHz or 3 GHz), and is locked by the output of the PLL subsystem at pin CP. Gain from the clock input to the outputs can be as much as 12 dB, in 1 dB steps.

Figure 5:
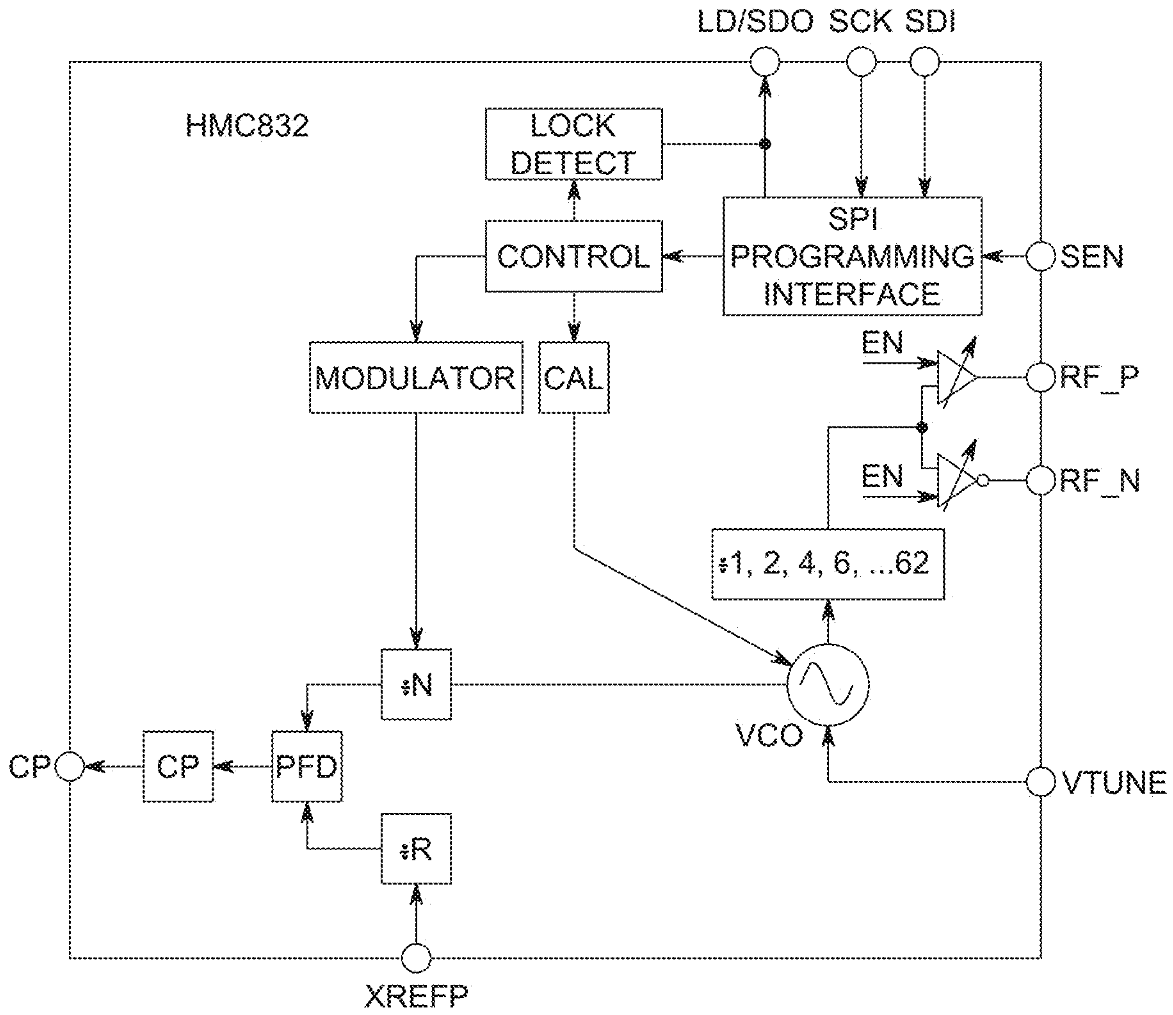
FIG. 5 is a block diagram of an exemplary PLL chip.

FIG. 5 is a functional block diagram from of the PLL 250. In this embodiment, SEN, the enabling pin connected to PLLC_CHP_En of FIG. 4, can be used by the MCU, external switches, or the like to turn the PLL 252 circuit off without affecting the VCO. An HMC 83LPSGE chip, for example, is a fractional-N PLL with integrated VCO chip. Accordingly, the SDI, SCK, and SDO pins can be used to select a frequency multiplying parameter R as well as to choose a frequency divider parameter N, so it is possible to arbitrarily set an output modulation frequency across pins PLLC_RF_N_OUT and PLLC_RF_P_OUT of FIG. 3 over a large range of frequencies through at least 3 GHz. The VCO subsystem controls the output stage of the chip, which through selection of R and N is capable of modulation frequencies from 25 Mhz to 3 GHz. PLLs with integrated VCOs generally exhibit integer boundary spurs at harmonics of the reference frequency, so a loop filter may be used between CP and VTUNE to quickly settle the output modulation when changing frequencies. One example of a loop filter is shown and described in FIG. 10.

Figure 6:
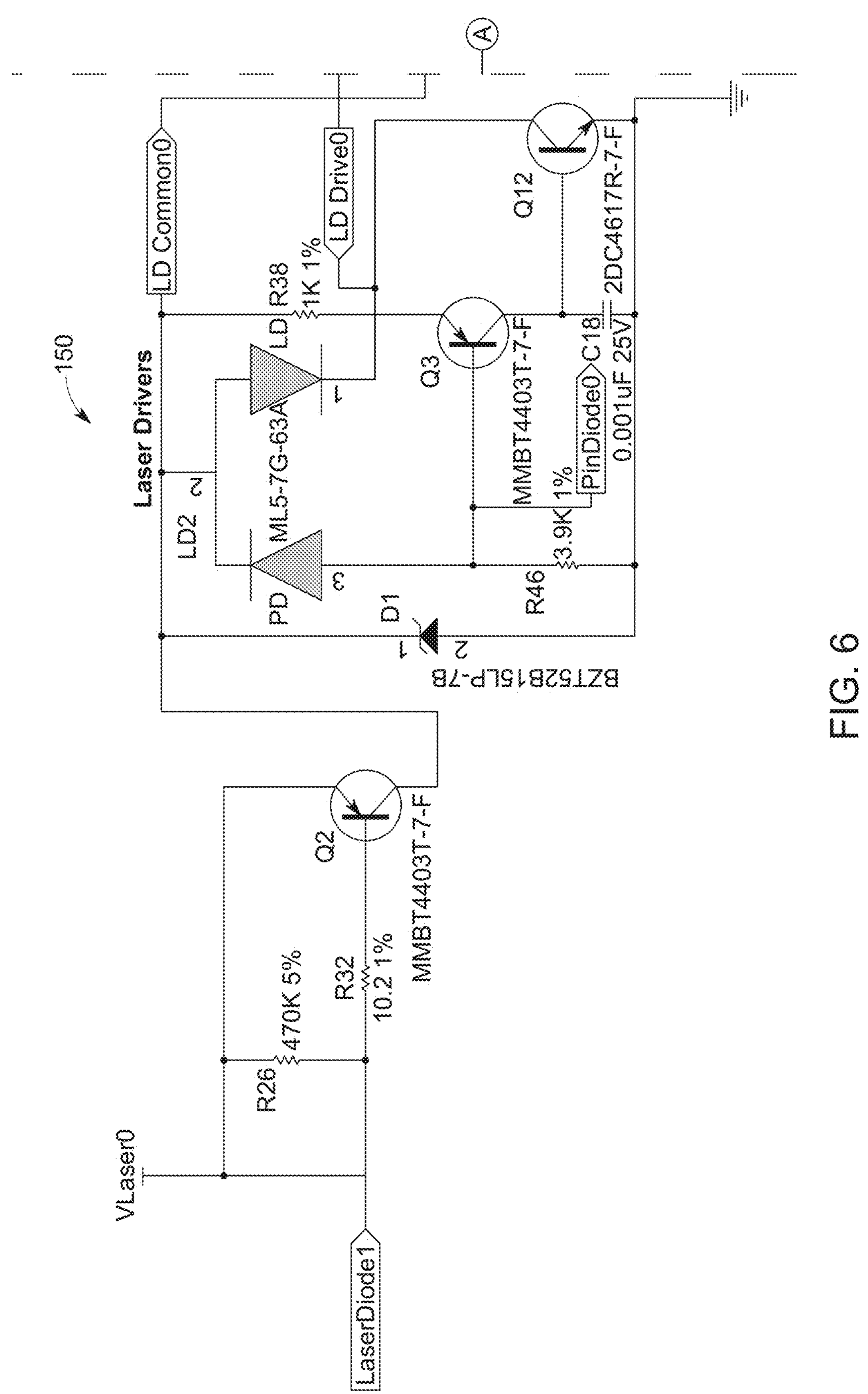
FIG. 6 illustrates one exemplary embodiment of a switchable low-pulse rate/high-pulse rate laser diode driver, and a laser diode module which can be driven at pulse rates from DC to 4 Gigahertz and higher.
Figure 6:
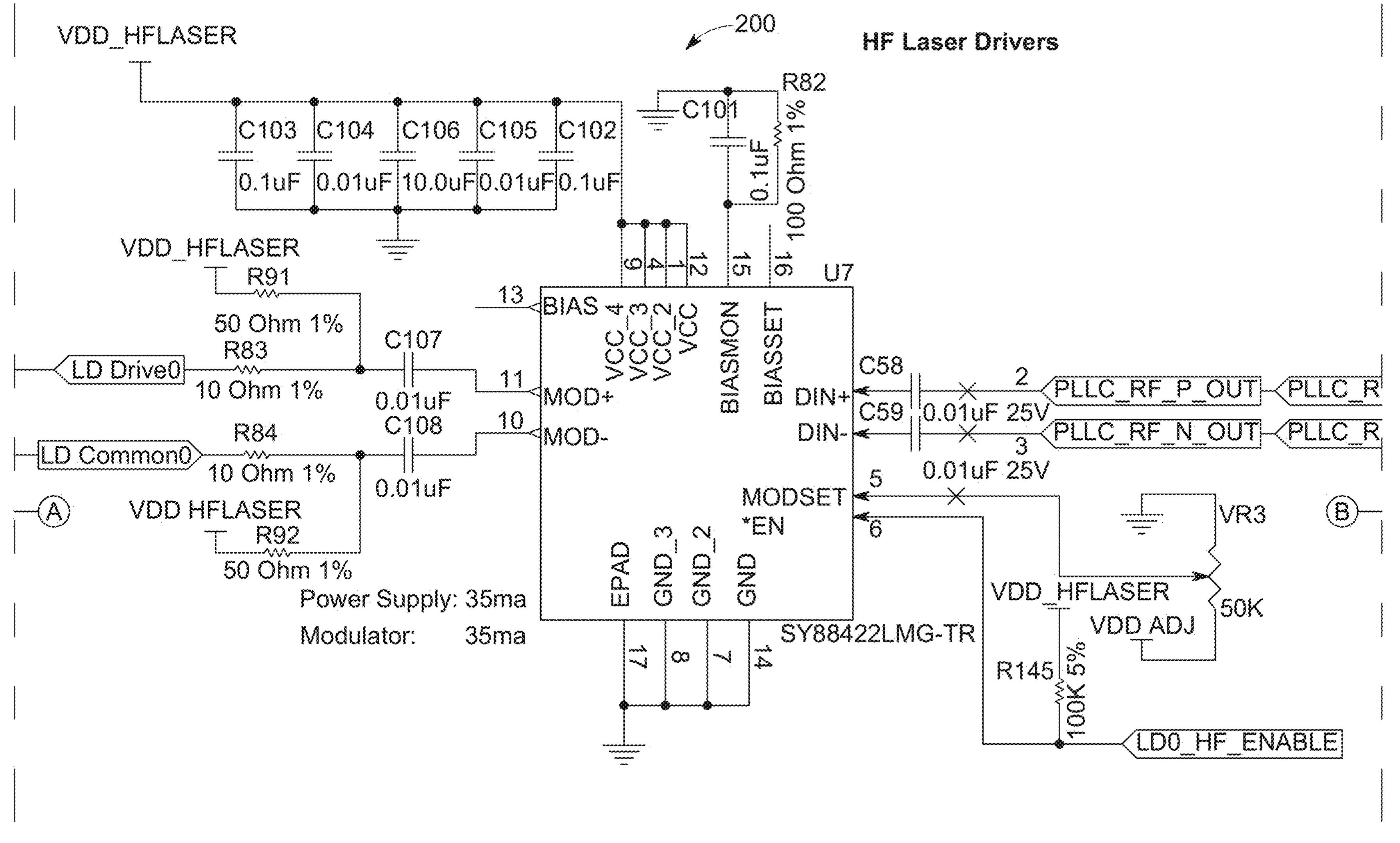
Figure 6:
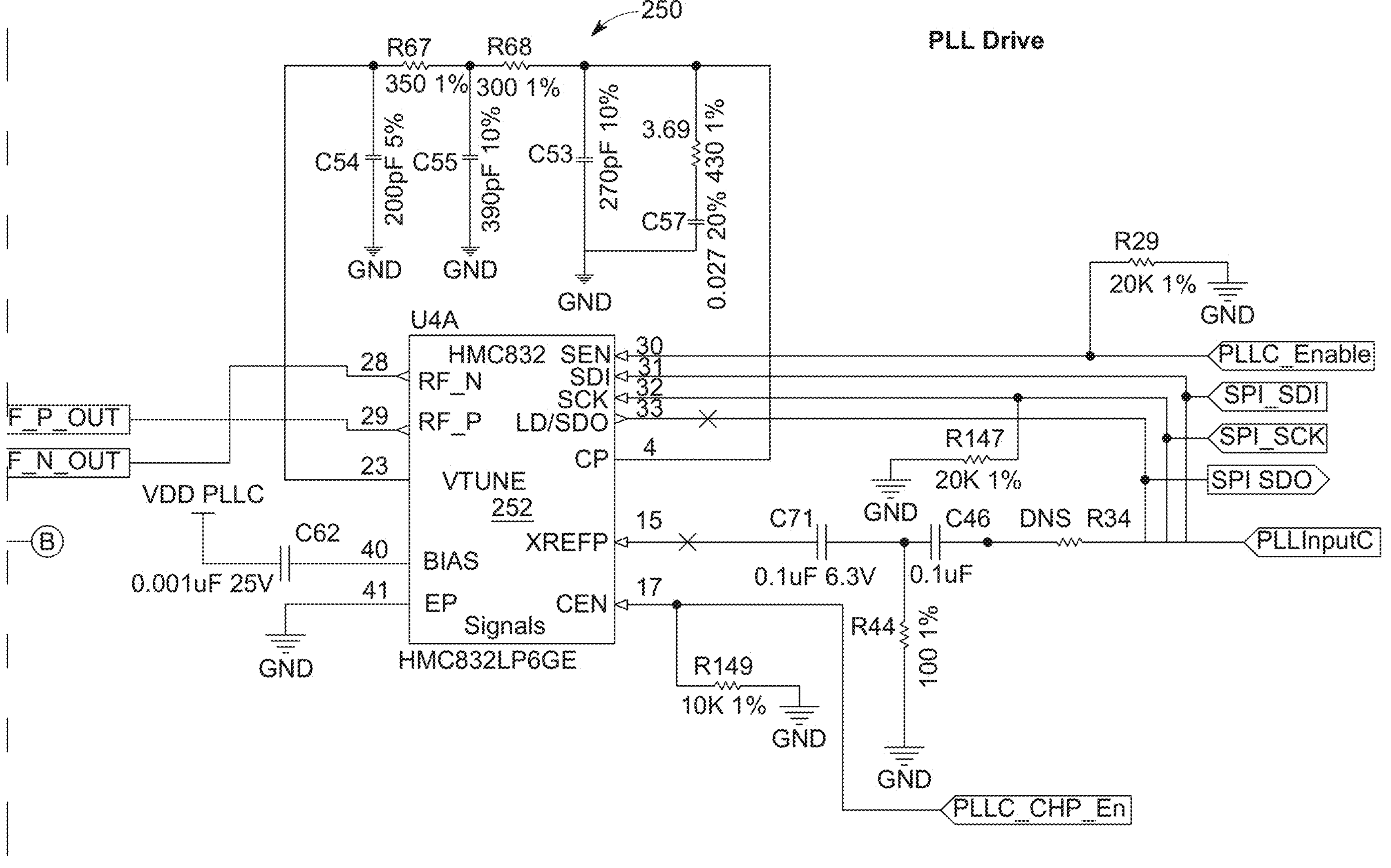

FIG. 6 illustrates one non-limiting, exemplary block diagram with the three circuits that can be used to provide laser diode pulses with consistent optical intensity and energy at rates from DC to 3 GHz. This embodiment can support a modulation of the laser pulses 110 from laser diode LD of FIG. 2 from DC up to 250 MHz. In this embodiment, C18 of FIG. 2 acts as a low pass filter when operating in the high pulse rate regime and suppresses ripple. At 300 Mhz, the duty cycle for this embodiment has moved from 50-50 on-off to 60-40 on-off, or more. Those skilled in the art will readily recognize that a different design could be used to support approximately 50-50 duty cycles for higher frequencies.

For cold laser therapy purposes, outputting pulses of the maximum safe laser diode intensity (e.g., approximately 5 mW) and approximately 50% duty cycle is the most commonly desired protocol, and it is possible, without loss of generality about other protocols or methods, to program the MCU to select the device to use the combined driver circuit in FIG. 6 to operate in the low-pulse-rate regime at an arbitrary pulse rate by disabling the high pulse rate driver 200, the driver 200 and the PLL 252, or the driver 200, PLL 252, and VCO, and/or by driving the input to the laser driver 150, LaserDiode0, with the appropriate modulation frequency. And, by alternatively selecting the device to operate in the high-pulse-rate regime, the laser diode system may: enable the "DC" mode of the laser driver 150 by holding LaserDiode0 low; enable PLL Driver (and thus the VCO);

use signals to the pins SPI SDI, SCK, SDO, as well as the SEN pin driven by PLLC_Enable, to set both R and N for the PLL and the VCO to select the high pulse rate; and/or enable the HF driver 200 via LDO_ENABLE.

It is also possible to reduce the power use of this circuit and achieve the same results by dropping power to the power plane for the high pulse rate driver VDD HFLASER, or both the power planes for the high pulse rate driver VDD HFLASER and the PLL driver VDD PLL.

In some embodiments, it is possible to select the components to bias the low pulse rate laser driver circuit, and additionally to select the RC time constant of R46 and C18 of FIG. 2 such that no frequency-dependent changes occur to the error signal at PinDiode0. In this regard, the full laser optical power is available, with an approximately 50-50 duty cycle, well above 25 Mhz, while additionally holding the low pulse rate driver circuit "on" by holding LaserDiode0 low and enabling the high pulse rate driver circuit and PLL driver to deliver full laser optical power with an approximately 50-50 duty cycle, down to 25 Mhz. Thus, it is possible to select a "change-over" frequency in the "overlap" such that the desired behavior is available at any selected frequency. Those skilled in the art will readily recognize how this, or similar circuitry and methods, can be used to vary duty cycles, optical intensity, and energy.

Figure 7:
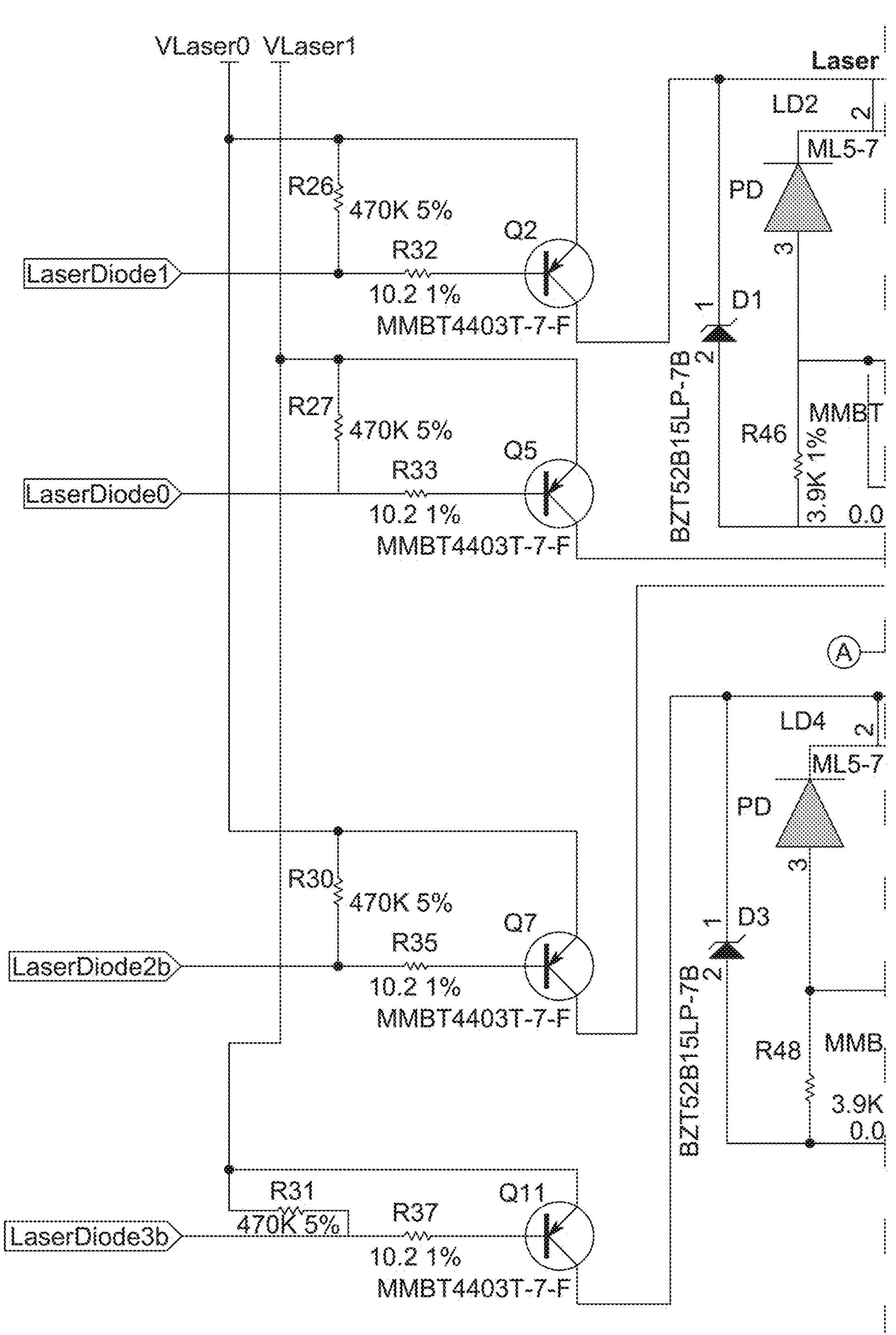
FIG. 7 illustrates one exemplary subsystem architecture for driving multiple laser diodes and photodiode modules.
Figure 7:
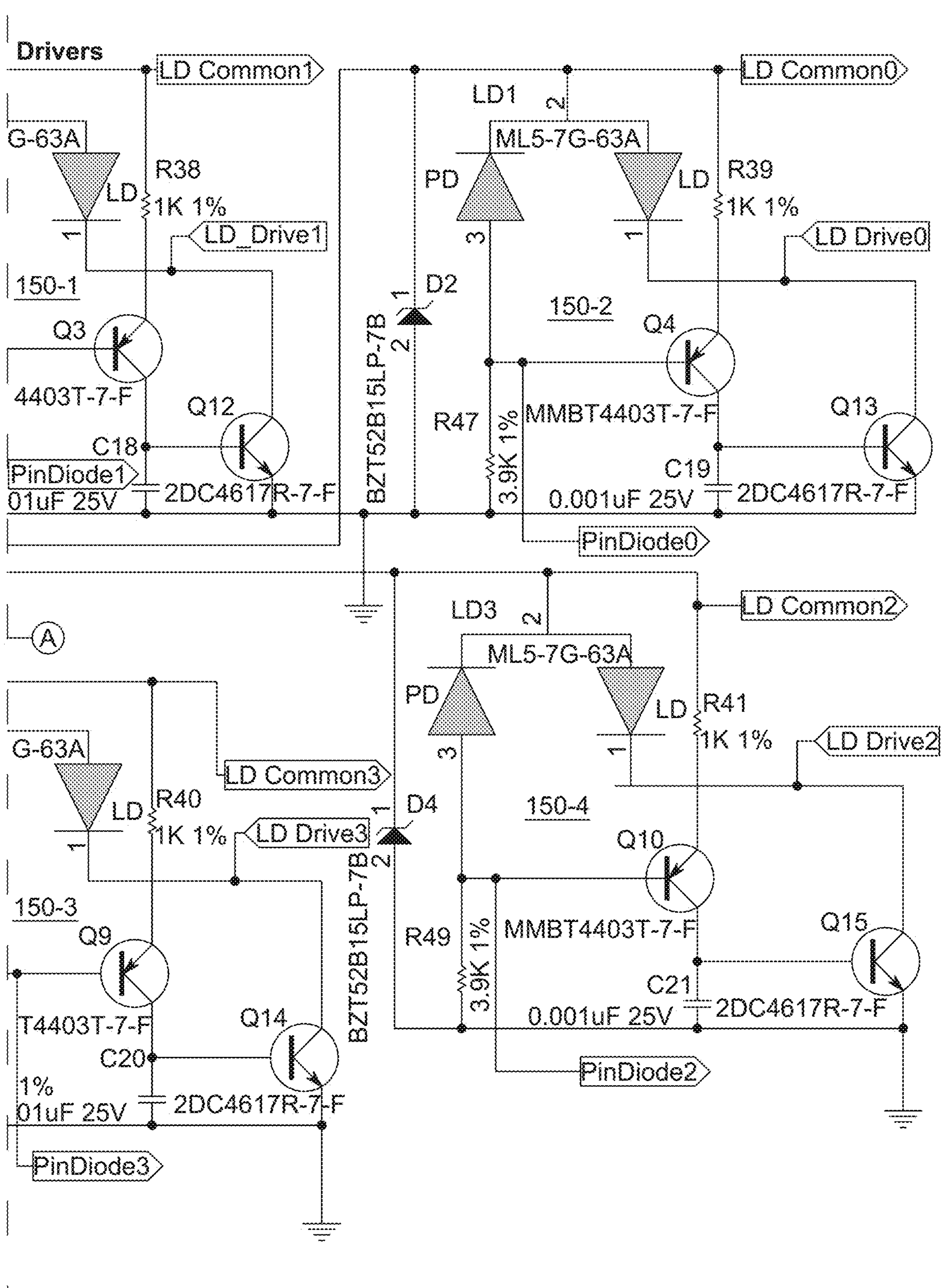
Figure 8:
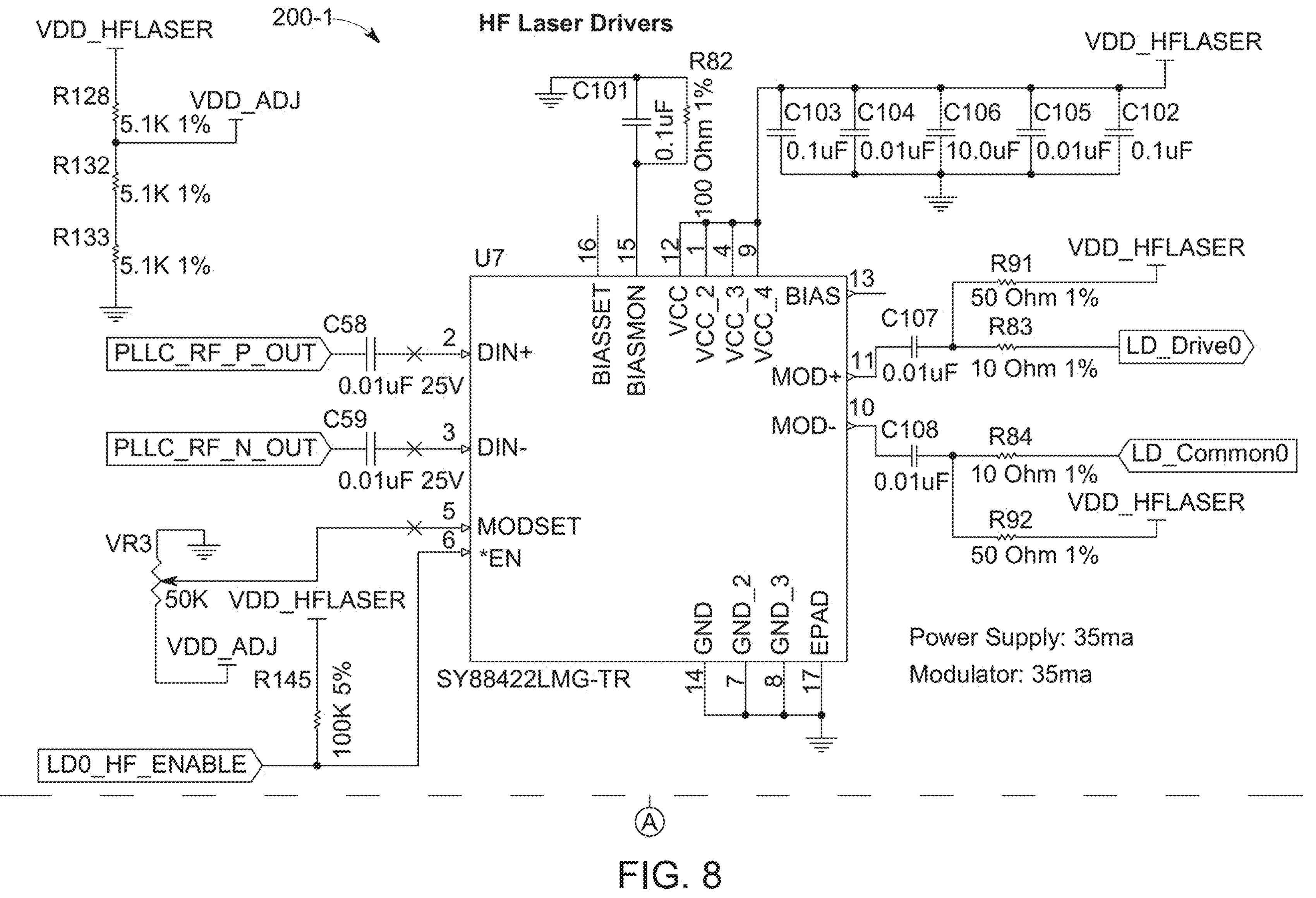
FIG. 8 illustrates one exemplary subsystem architecture for using high pulse rate differential laser driver subsystems for driving multiple laser diode and photodiode modules.
Figure 8:
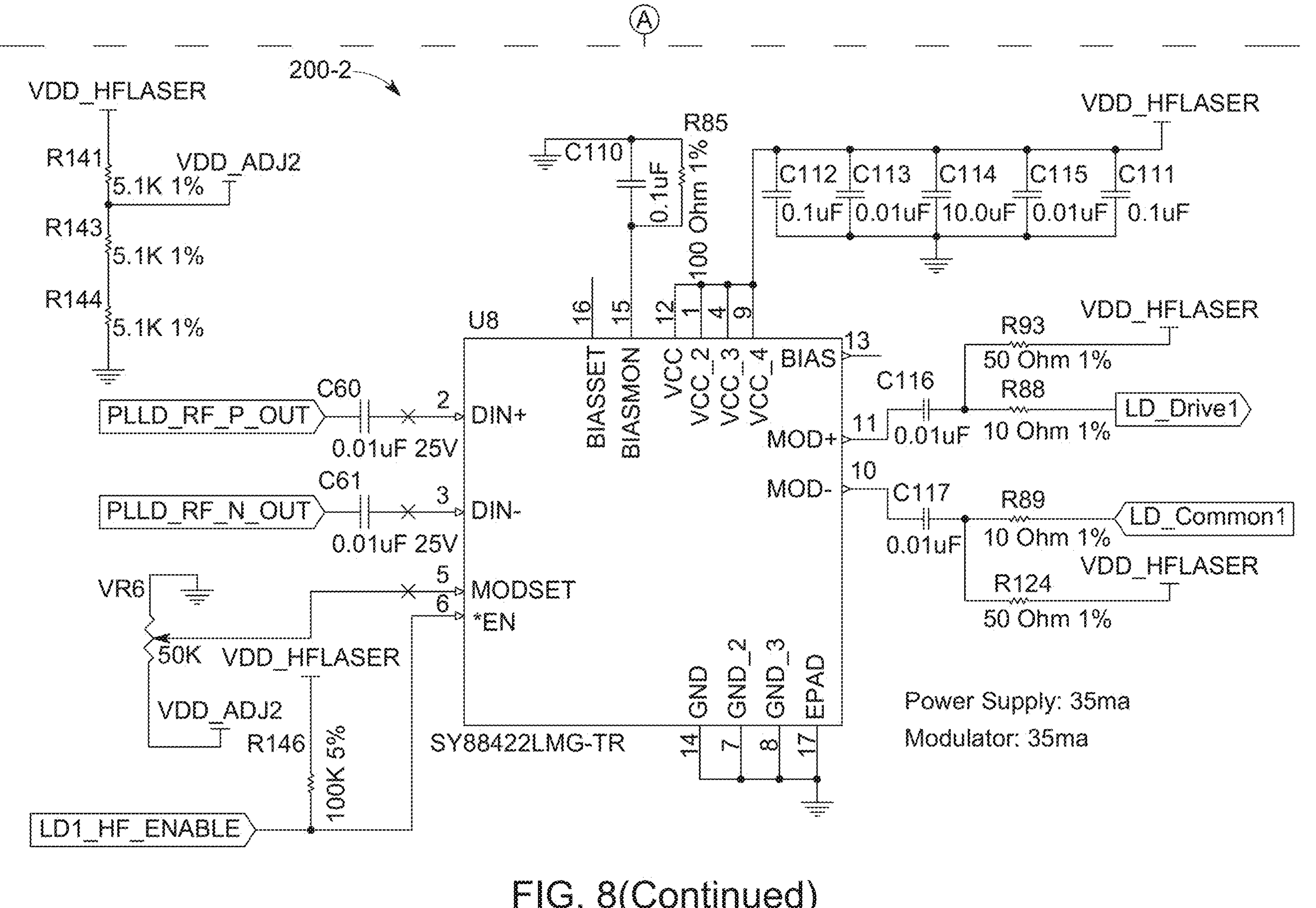
Figure 9:
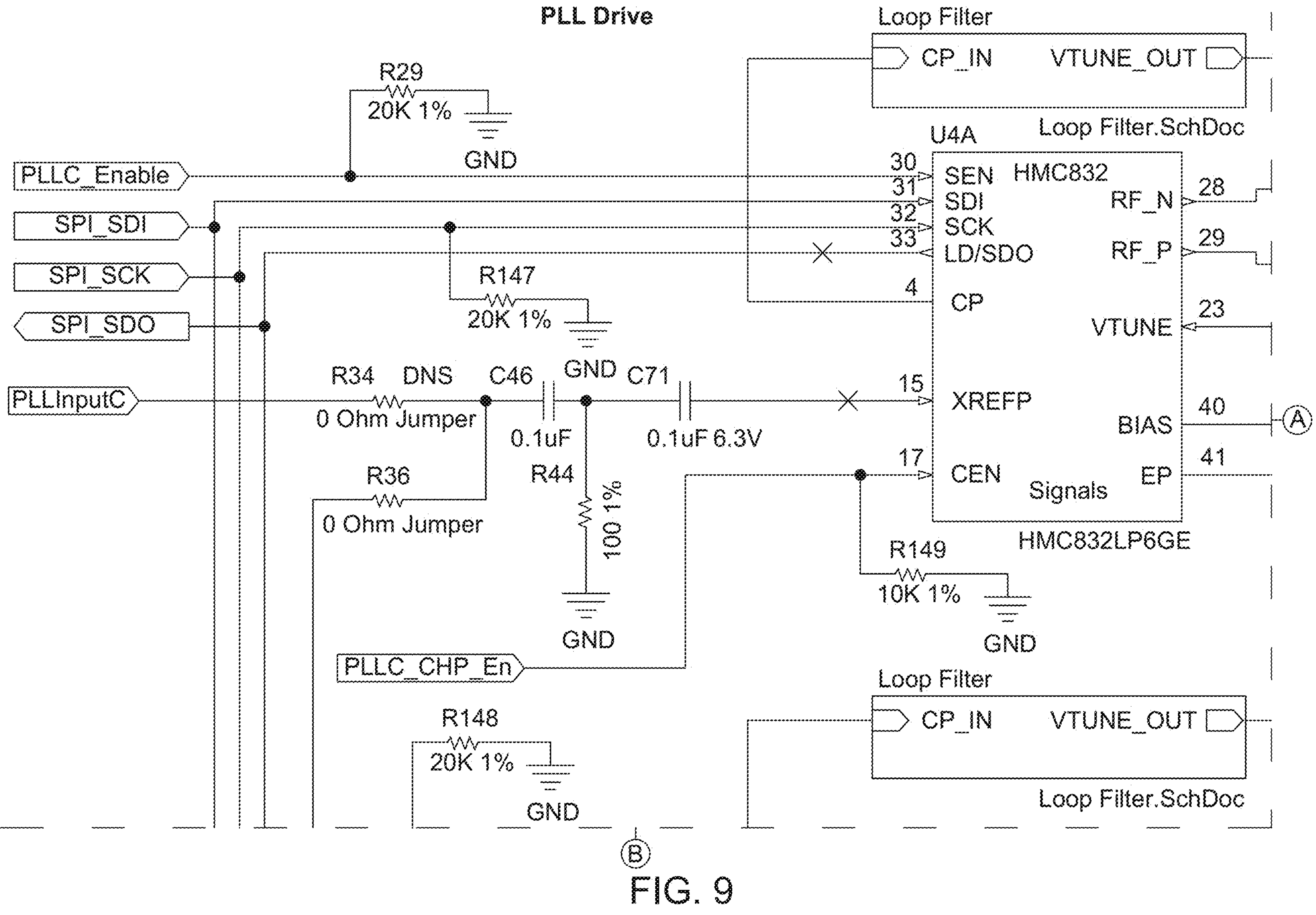
FIG. 9 illustrates one exemplary subsystem architecture for using PLL modulation drive subsystems for driving multiple laser diode and photodiode modules.
Figure 9:
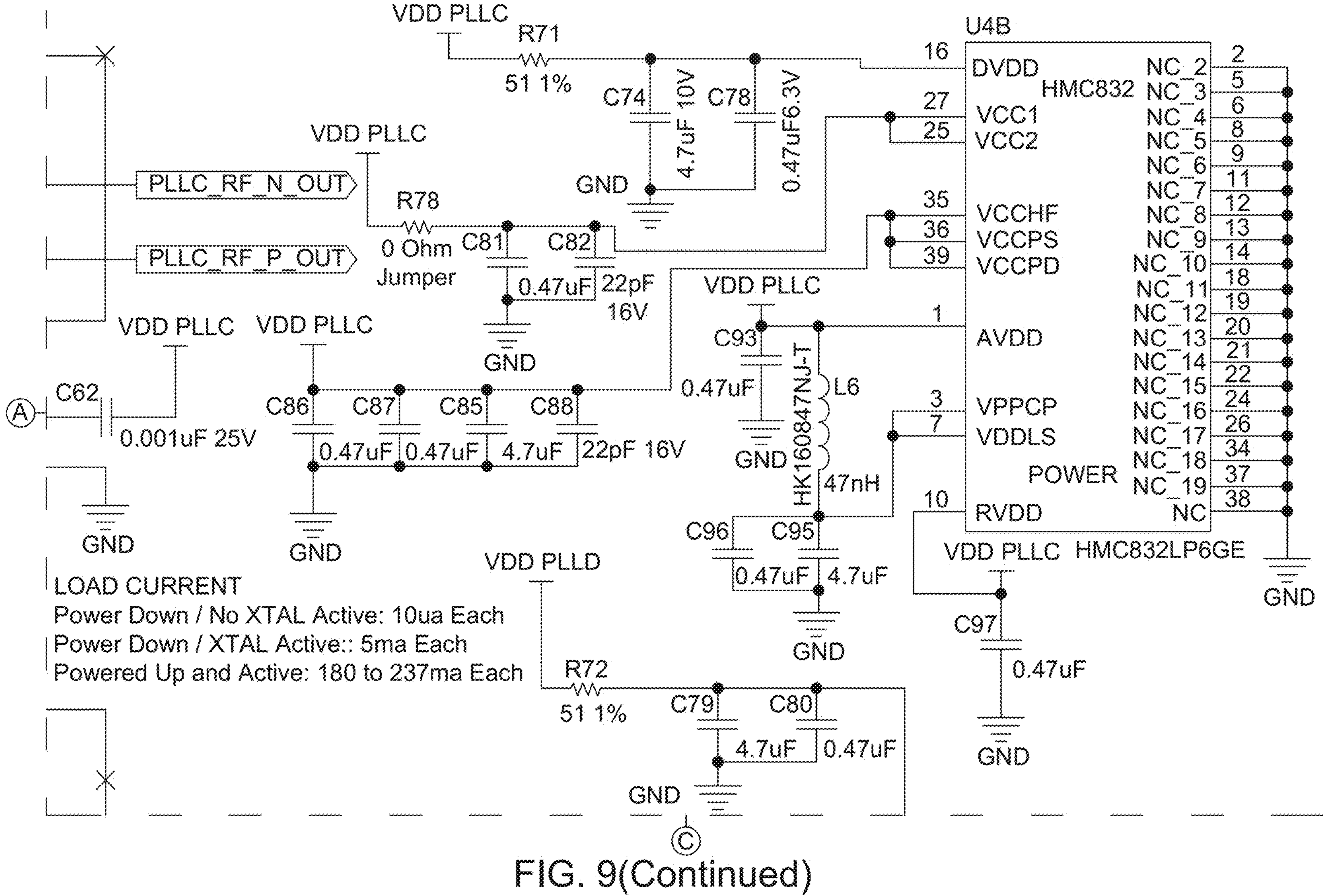
Figure 9:
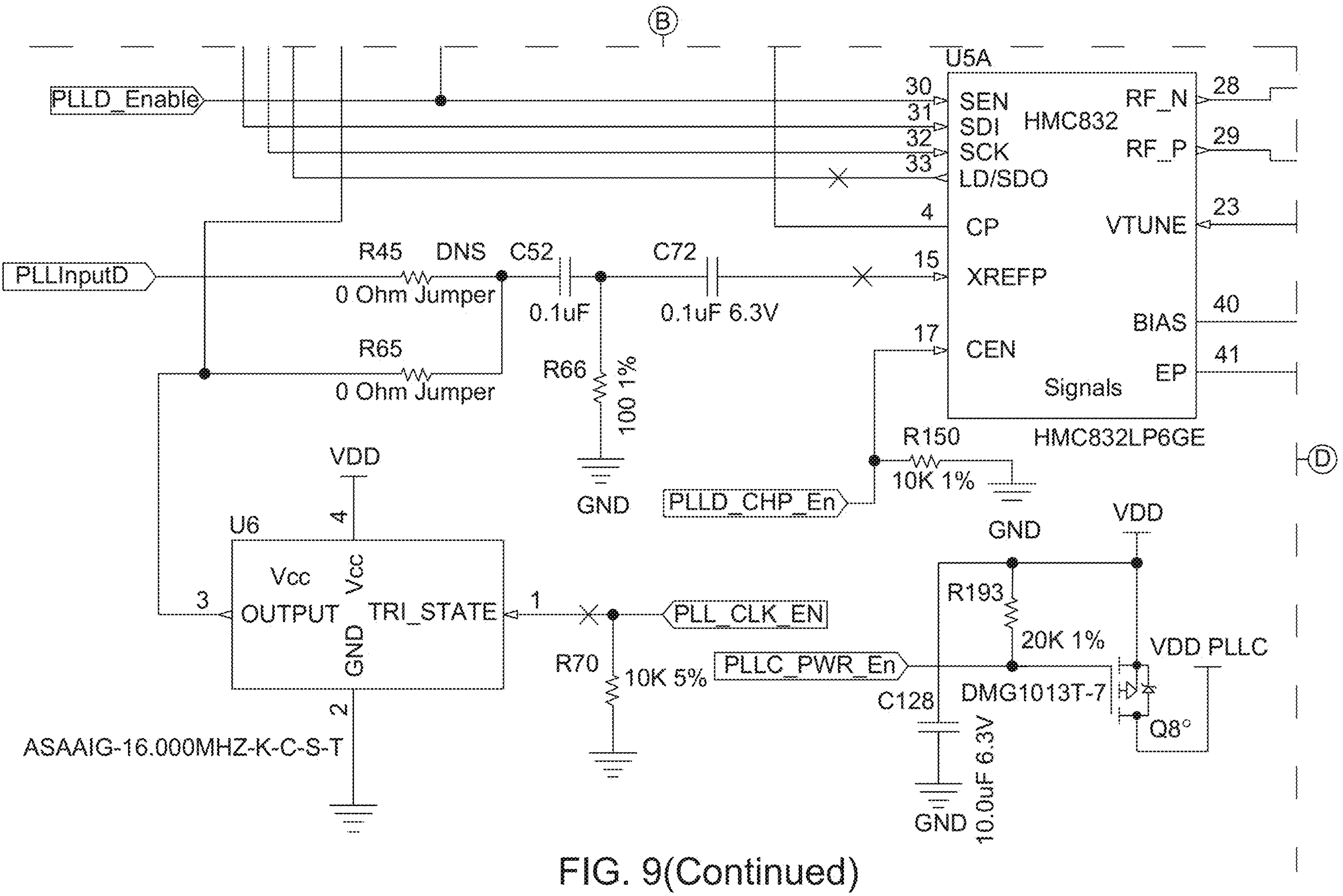
Figure 9:
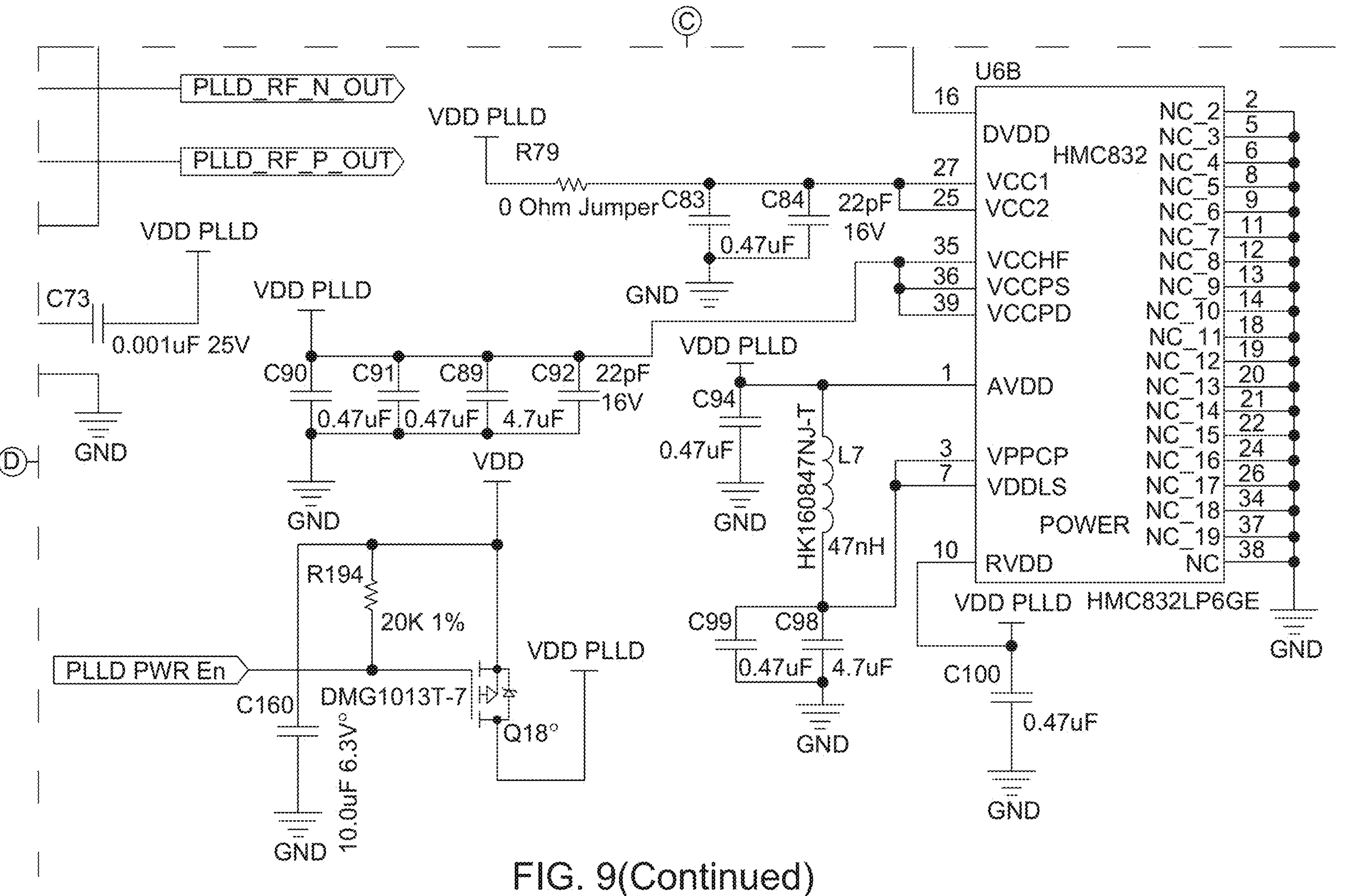

FIGS. 7-9 illustrate, non-limiting exemplary embodiments how an array of laser diodes can be driven by circuitry composed of all the same elements to effect cold laser treatments with identical protocols for each laser diode resulting in treatment over a larger area. This is generally desirable because it can reduce the time that a treatment requires. Alternatively, dissimilar protocols (e.g., combinations of various low and/or high pulse rates) may also be used. This arrangement saves treatment time via simultaneous treatment with multiple protocols, while similarly using the "change-over" frequency to determine the necessary pulse rate regime for driving any of the laser diodes.

Figure 10:
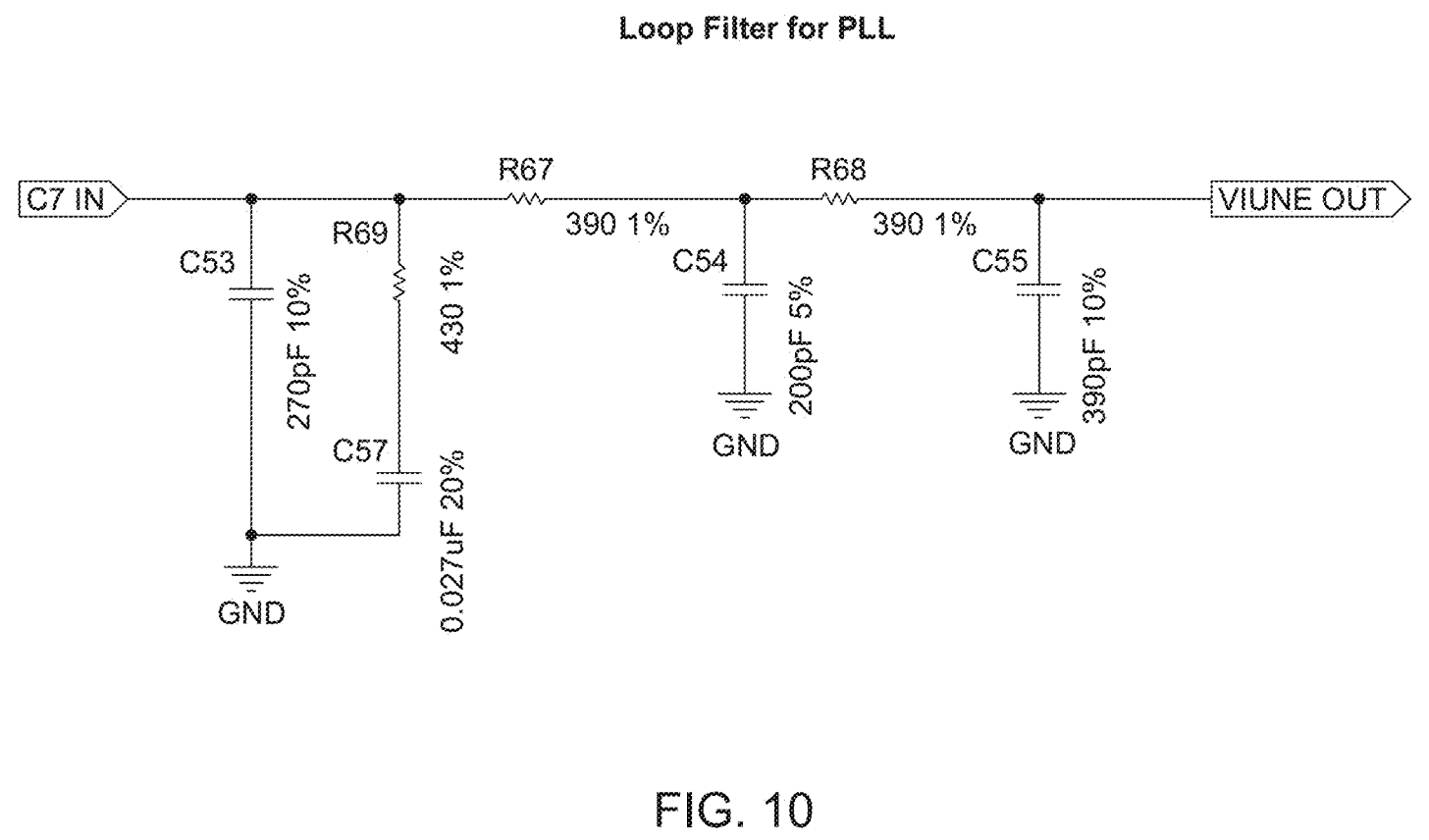

FIG. 10 is a block diagram of one exemplary loop filter from FIGS. 6 and 9, included for clarity.

Figure 11:
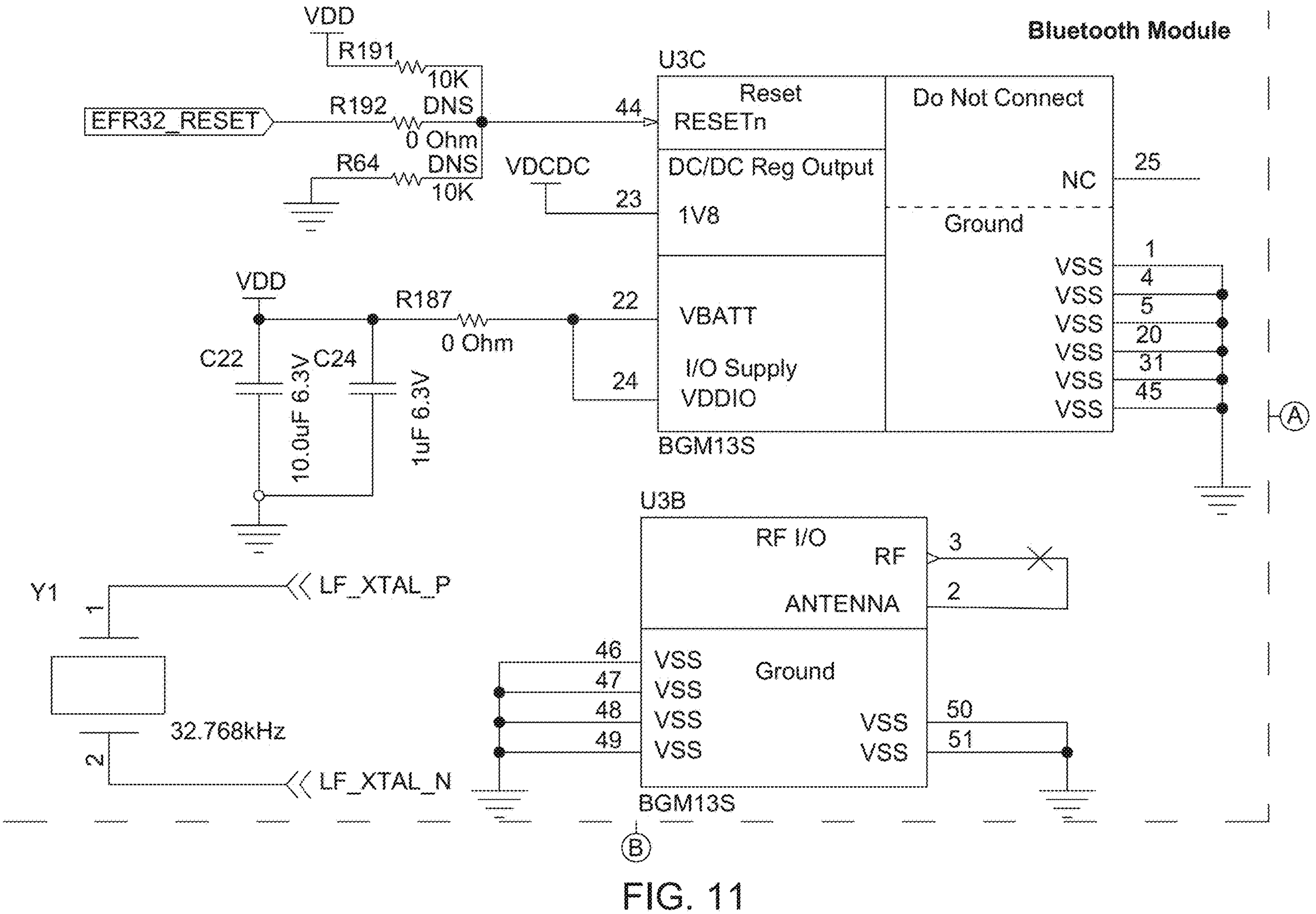
FIG. 11 illustrates exemplary embodiments of extended functionalities with Bluetooth wireless connectivity, inertial measurement via an IMU, external firmware programmability and re-programmability, and flash memory.
Figure 11:
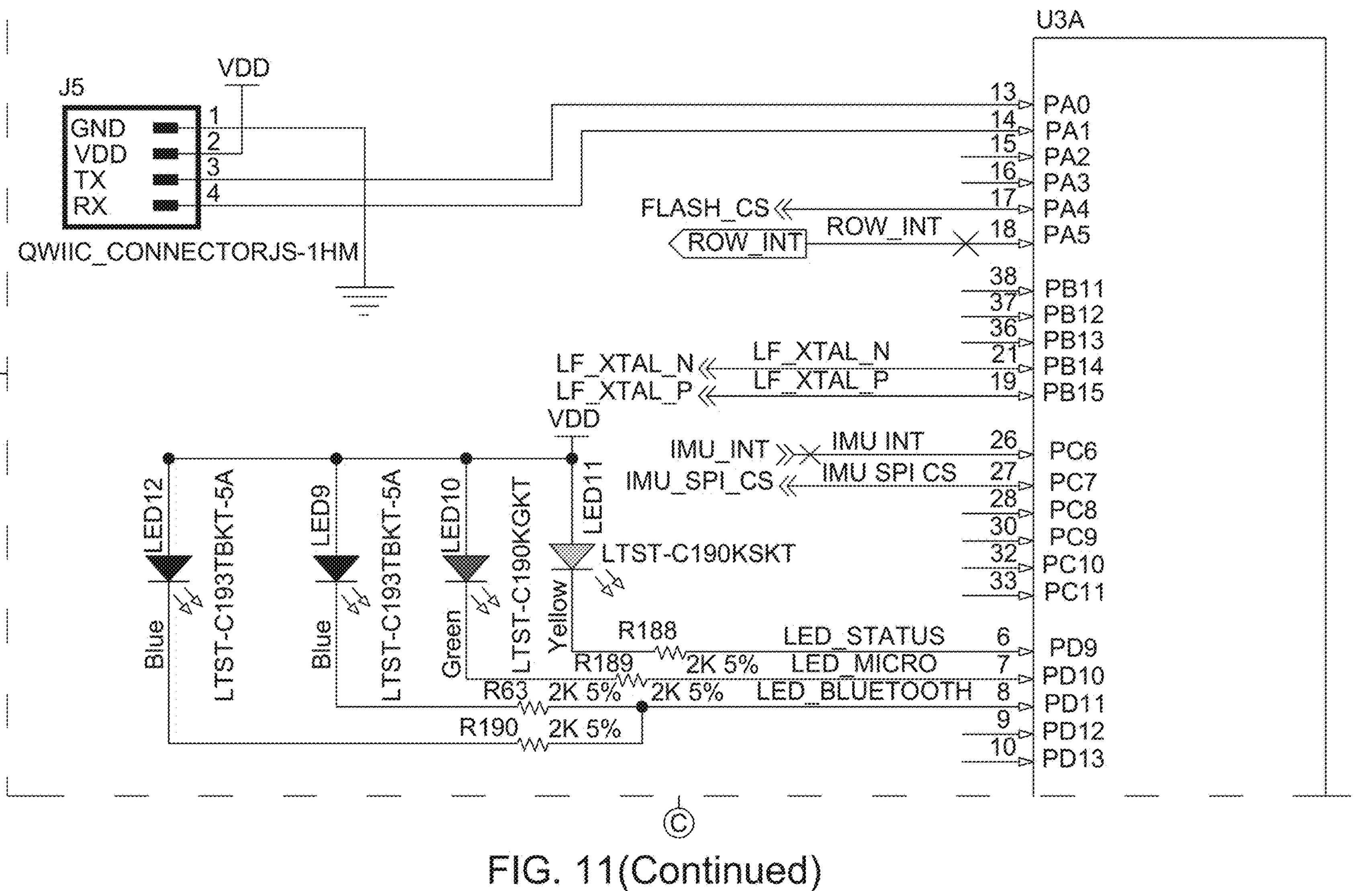
Figure 11:
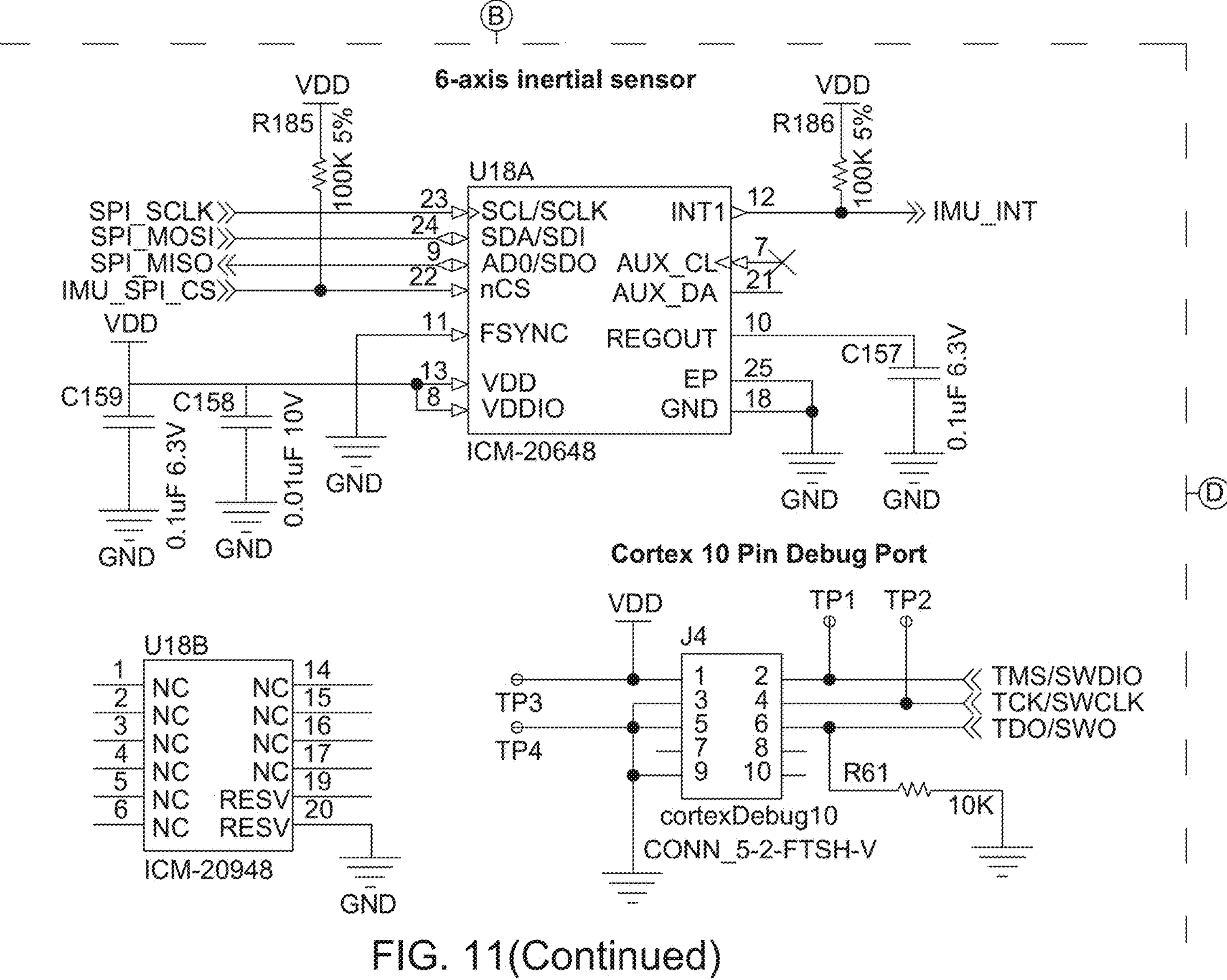
Figure 11:
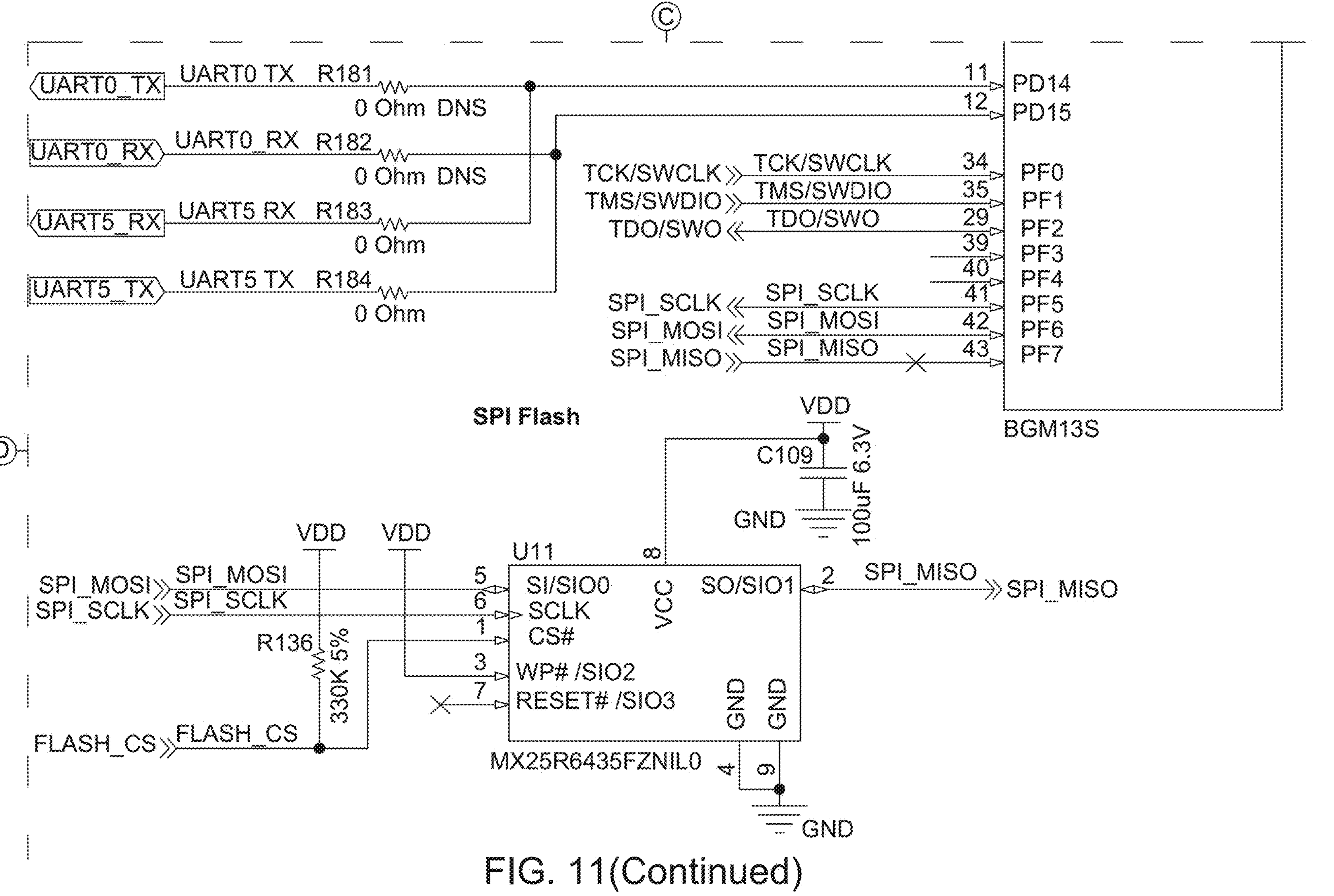

FIG. 11 illustrates one non-limiting, embodiment wherein Bluetooth connectivity, device inertial motion sensing, flash memory, and cabled programming debug abilities may be added to the laser system. For example, treatment by a doctor in their office is not a requirement, and many patients prefer to own their devices so that treatments can be made, as necessary. However, distributed use of such equipment also means that it is desirable to perform firmware upgrades, add in new protocols, and debug the devices, if not by the user, then locally or at a repair center. In this embodiment, these abilities are instantiated by a Cortex 10 pin debug port J4, a QWIIC connector connection socket J5, and various colored light emitting diodes LED9, LED10, LED11, and LED12.

Including additional capabilities into the device opens up many applications for telehealth, remote treatment, VR systems, AI patient interaction systems, and/or outcome analysis systems. For example, Bluetooth wireless flow of treatment information both to and from the device enables a medical professional, healthcare assistant, or family member to monitor the device use remotely. In some embodiments, wireless Bluetooth communications are instantiated via a Bluegiga module BGM13S U3B and U3C, and a crystal/resonator Y1.

Adding in non-volatile memory allows the device to receive and safely use over the air firmware updates for embedded system components such as MCUs, new transmission protocols, and/or to save new treatment protocols on the device. Here the memory is instantiated via a Macronix 64 megabit flash memory chip, but other devices may be used.

Adding in the ability to sense device information and either storing it in memory, or transmitting it in real-time, is useful for applications in remote treatment, VR systems, AI patient interaction systems, and/or as outcome analysis systems. Here, a six-axis inertial sensor (e.g., a triplet of accelerometers and a triplet of rate gyros) is used in combination with the MCU in the BGM13S to create an IMU. But nine-axis IMUs and other forms of sensors (e.g., cameras, ambient temperature and irradiance sensors, microphones, battery sensors, etc.) can be useful in such applications. For example, a doctor might transmit a new treatment protocol to a remote device, and use a virtual reality rig to "see" precisely how a patient or caregiver operates the treatment device. Or the patient/caregiver might similarly use a VR rig and a cold laser treatment device with an IMU, to have feedback on where and how long they should apply treatment.

Serial communication can be implemented via Bluetooth (e.g., run in a serial "cable replacement mode") and/or actual cables. Serial connections can be made to the MCU, or it can be tied from the BGM13S module. Such serial connections and communications would include transmission of sensor telemetry, including but not limited to data from the sensors, such as IMU data.

The wide range of potential therapeutic pulse rates can be useful for outcome analysis. Additionally, remote treatments using robotic arms and similar methods generally require feedback from the devices to function. This could be combined with, for example, an AI assistant that gathers patient information, and/or that disseminates medical information about a treatment in order to assist in remote treatment, and/or to accurately measure treatment outcomes.

Figure 12:
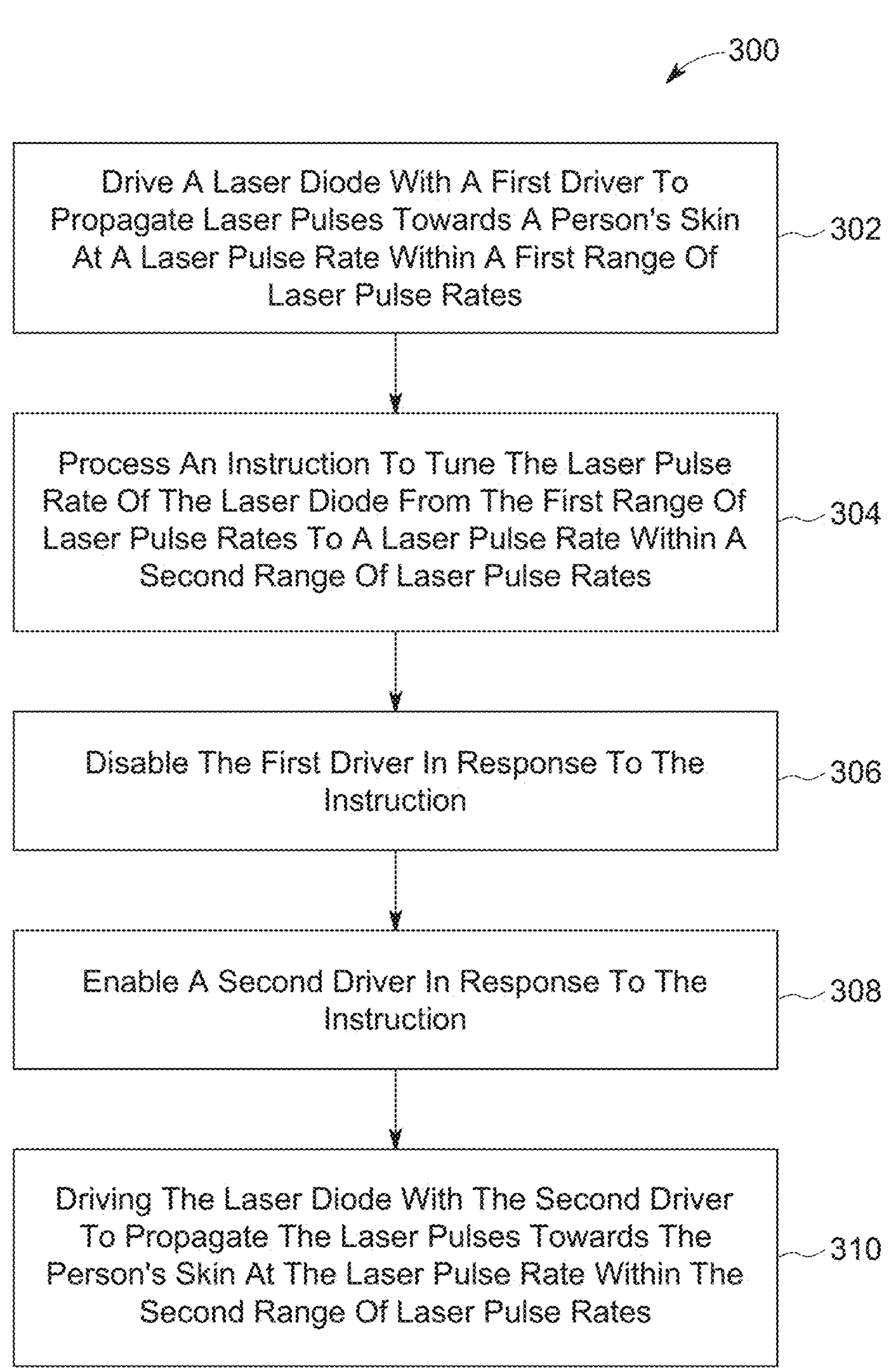
FIG. 12 is a flowchart of an exemplary process of the embodiments shown or described herein.

FIG. 12 is a flowchart of one exemplary process 300 of the embodiments shown and described herein. In this embodiment, a cold laser therapy device is implemented with a controller 102, a low-frequency driver 104, a high-frequency driver 106, and a laser diode 108, as shown and described in FIG. 1. The device may be turned on via some input to the controller 102 (e.g., a switch, and on off button, etc.). Then, a user of the device, according to some medical protocol for using the device, may instruct the device to begin pulsed cold laser therapy in either the low-frequency pulse rate range or the high-frequency pulse rate range. For example, a user may provide a pulse rate input to the controller 102 (e.g., via a switch, a pulse rate dial, etc.) that directs the low-frequency driver 104 to drive the laser diode 108 at a pulse rate within the low-frequency pulse rate range (e.g., between about 0 Hz and 50 MHz), in the process element 302. The laser diode 108 response by delivering laser pulses 110 to a person's skin at the desired pulse rate within the lower pulse rate range.

Then, a change in the cold laser therapy protocol may call for a pulse rate within a high-frequency pulse rate range. In this regard, the user may input a desired pulse rate into the device that is outside the range of the low-frequency driver 104. In this regard, the pulse rate change operates as an instruction to the controller 102 to tune the laser pulse rate of the laser diode 108 from the low-frequency pulse rate range to the high-frequency pulse rate range of the high-frequency driver 106 (e.g., between about 50 MHz and 4 GHz), in the process element 304. In response to the instruction, the controller 102 may disable the first/low-frequency driver 104, in the process element 306, and enable the second/high-frequency driver 106, in the process element 308. Thereafter, the high-frequency driver 106 begins driving the laser diode 108 to propagate the laser pulses 110 to the person's skin at the selected pulse rate within the high-frequency pulse rate range, in the process element 310.

It should be noted that the initial pulse rate could be within either the lower pulse rate range or the higher pulse rate range according to the cold laser therapy protocol being implemented. It should also be noted that the desired pulse rate may be input to the cold laser therapy device the other means (e.g., wireless communications, Internet communications, etc.) as part of a remote cold laser therapy procedure. Additionally, while a duty cycle of 50% is often preferred, duty cycles of the laser pulses 110 may be selected as a matter of design choice and implemented via the controller 102 as instructed by the user of the cold laser therapy device.

While the embodiments have been illustrated and described in detail in the drawings and foregoing description, such illustration and description are to be considered as exemplary and not restrictive in character. Certain embodiments described herein may be combinable with other described embodiments and/or arranged in other ways. Accordingly, it should be understood that only certain embodiments and variants thereof have been shown and described and that all changes and modifications that come within their scope and spirit are desired to be protected.

Figure 13:
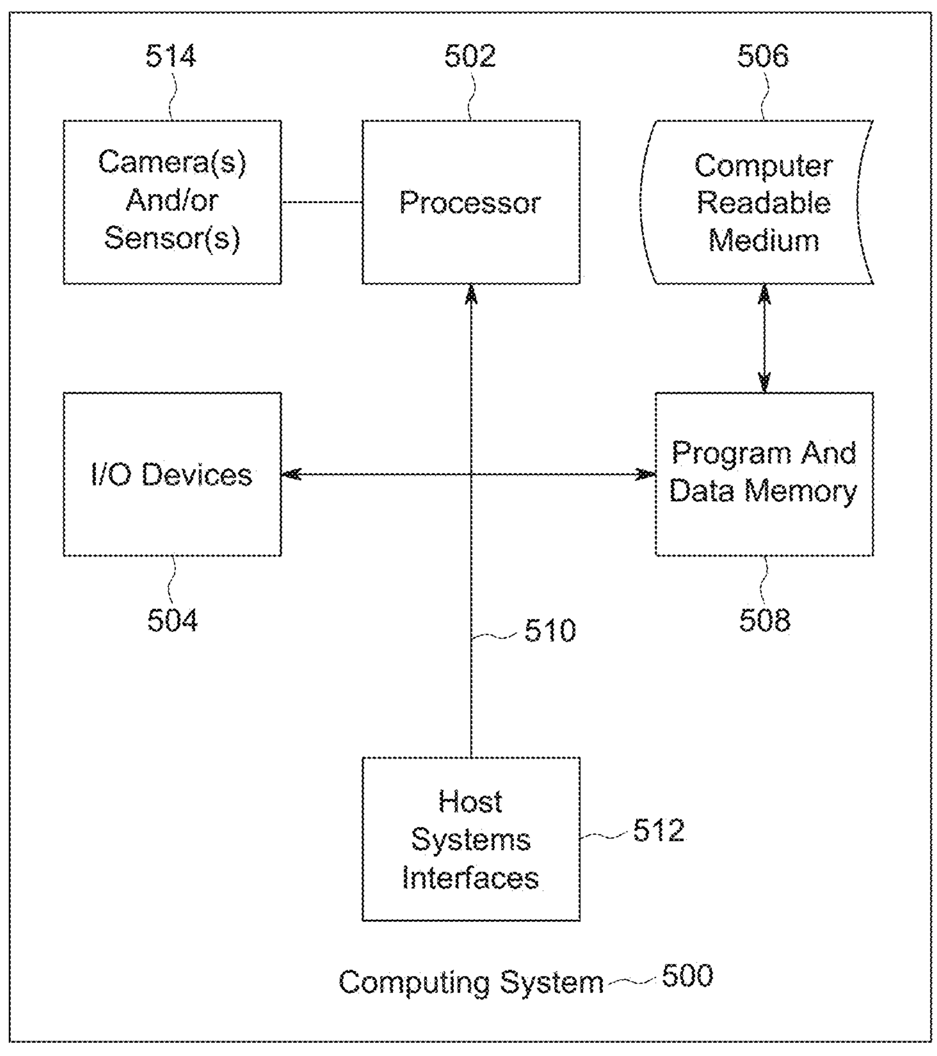
FIG. 13 is a block diagram of an exemplary computing system in which a computer readable medium provides instructions for performing methods herein.

Additionally, the embodiments can take the form of entirely hardware or comprising both hardware and software elements. Portions of the embodiments may be implemented in software, which includes but is not limited to firmware, resident software, microcode, etc. FIG. 13 illustrates a computing system 500 in which a computer readable medium 506 may provide instructions for performing any of the methods disclosed herein.

Furthermore, the embodiments can take the form of a computer program product accessible from the computer readable medium 506 providing program code for use by or in connection with a computer or any instruction execution system. For the purposes of this description, the computer readable medium 506 can be any apparatus that can tangibly store the program for use by or in connection with the instruction execution system, apparatus, or device, including the computer system 500.

The medium 506 can be any tangible electronic, magnetic, optical, electromagnetic, infrared, or semiconductor system (or apparatus or device). Examples of a computer readable medium 506 include a semiconductor or solid state memory, magnetic tape, a removable computer diskette, a random access memory (RAM), NAND flash memory, a read-only memory (ROM), a rigid magnetic disk and an optical disk. Some examples of optical disks include compact disk-read only memory (CD-ROM), compact disk-read/write (CD-R/W) and digital versatile disc (DVD).

The computing system 500, suitable for storing and/or executing program code, can include one or more processors 502 coupled directly or indirectly to memory 508 through a system bus 510. The memory 508 can include local memory employed during actual execution of the program code, bulk storage, and cache memories which provide temporary storage of at least some program code in order to reduce the number of times code is retrieved from bulk storage during execution. Input/output or I/O devices 504 (including but not limited to keyboards, displays, pointing devices, etc.) can be coupled to the system either directly or through intervening I/O controllers. Network adapters may also be coupled to the system to enable the computing system 500 to become coupled to other data processing systems, such as through host systems interfaces 512, or remote printers or storage devices through intervening private or public networks. Modems, cable modem and Ethernet cards are just a few of the currently available types of network adapters.

What is claimed is:

1. A cold laser therapy device, comprising:

a laser diode operable to propagate laser pulses towards a person's skin;

a first driver operable to drive the diode laser to propagate the laser pulses within a first range of laser pulse rates;

a second driver operable to drive the diode laser to propagate the laser pulses within a second range of laser pulse rates, wherein the second range of laser pulse rates is higher than the first range of laser pulse rates; and a controller operable to process an instruction to tune a laser pulse rate of the diode laser from the first range of the laser pulse rates to the second range of the laser pulse rates, to disable the first driver in response to the instruction, and to enable the second driver in response to the instruction.

2. The device of claim 1, wherein:

the controller is further operable to receive another instruction to tune the laser pulse rate of the diode laser from the second range of the laser pulse rates to the first range of the laser pulse rates, to disable the second driver in response to the instruction, and to enable the first driver in response to the instruction.

3. The device of claim 1, wherein:

the first driver comprises a feedback circuit that is operable to control optical energy of the laser pulses from the diode laser.

4. The device of claim 3, wherein:

the optical energy is less than about 6 milliwatts.

5. The device of claim 1, wherein:

the first range of laser pulse rates is between zero Hz and 50 MHz.

6. The device of claim 1, wherein:

the second range of laser pulse rates is between 50 MHz and 4 GHz.

7. The device of claim 1, further comprising:

a phase locked loop controller operable to drive the second driver, and to maintain a constant pulse rate within the second range of laser pulse rates.

8. The device of claim 1, further comprising:

a wireless communication module operable to:

provide remote control to the device; and provide an interface for at least one of upgrading firmware to the device and communicating with a caregiver.

9. A method of operating a cold laser therapy device, the method comprising:

driving a diode laser with a first driver to propagate laser pulses towards a person's skin at a laser pulse rate within a first range of laser pulse rates;

processing an instruction to tune the laser pulse rate of the diode laser from the first range of laser pulse rates to a laser pulse rate within a second range of laser pulse rates, wherein the second range of laser pulse rates is higher than the first range of laser pulse rates;

disabling the first driver in response to the instruction;

enabling a second driver in response to the instruction; and driving the diode laser with the second driver to propagate the laser pulses towards the person's skin at the laser pulse rate within the second range of laser pulse rates.

10. The method of claim 9, further comprising:

receiving another instruction to tune the laser pulse rate of the diode laser from the second range of the laser pulse rates to the first range of the laser pulse rates;

disabling the second driver in response to the instruction; and enabling the first driver in response to the instruction.

11. The method of claim 9, further comprising:

processing a feedback signal to control optical energy of laser pulses from the diode laser.

12. The method of claim 11, wherein:

the optical energy is less than about 6 milliwatts.

13. The method of claim 9, wherein:

the first range of laser pulse rates is between about zero Hz and 50 MHz.

14. The method of claim 9, wherein:

the second range of laser pulse rates is between about 50 MHz and 4 GHz.

15. The method of claim 9, further comprising:

driving the second driver with a phase locked loop controller to maintain a constant pulse rate within the second range of laser pulse rates.

16. The method of claim 9, further comprising:

providing remote control to the device via a wireless communication module; and providing for at least one of upgrading firmware to the device and communicating with a caregiver via the wireless communication module.

17. A non-transitory computer readable medium comprising instructions that, when executed by a controller of a cold laser therapy device, direct the controller to:

drive a diode laser with a first driver to propagate laser pulses towards a person's skin at a laser pulse rate within a first range of laser pulse rates;

process an instruction to tune the laser pulse rate of the diode laser from the first range of laser pulse rates to a laser pulse rate within a second range of laser pulse rates, wherein the second range of laser pulse rates is higher than the first range of laser pulse rates;

disable the first driver in response to the instruction;

enable a second driver in response to the instruction; and drive the diode laser with the second driver to propagate the laser pulses towards the person's skin at the laser pulse rate within the second range of laser pulse rates.

* * * * *